(12) United States Patent
Ota et al.

(10) Patent No.: US 10,052,401 B2
(45) Date of Patent: Aug. 21, 2018

(54) ABSORBENT ARTICLE CONTAINING A WATER-ABSORBENT RESIN POWDER

(71) Applicant: LIVEDO CORPORATION, Shikokuchuo-shi, Ehime (JP)

(72) Inventors: Yoshihisa Ota, Mima-gun (JP); Motoko Nishida, Mima-gun (JP); Masatoshi Ikeuchi, Mima-gun (JP)

(73) Assignee: LIVEDO CORPORATION, Shikokuchuo-shi (JP)

( * ) Notice: Subject to any disclaimer, the term of this patent is extended or adjusted under 35 U.S.C. 154(b) by 334 days.

(21) Appl. No.: 14/368,886

(22) PCT Filed: Dec. 20, 2012

(86) PCT No.: PCT/JP2012/008170
§ 371 (c)(1),
(2) Date: Jun. 26, 2014

(87) PCT Pub. No.: WO2013/099175
PCT Pub. Date: Jul. 4, 2013

(65) Prior Publication Data
US 2014/0364824 A1 Dec. 11, 2014

(30) Foreign Application Priority Data
Dec. 27, 2011 (JP) .................. 2011-285292

(51) Int. Cl.
*A61F 13/15* (2006.01)
*A61F 13/20* (2006.01)
(Continued)

(52) U.S. Cl.
CPC .......... *A61L 15/60* (2013.01); *A61F 13/5323* (2013.01); *A61L 15/26* (2013.01); *A61L 15/42* (2013.01); *A61L 2300/20* (2013.01)

(58) Field of Classification Search
CPC ....... A61F 13/5323; A61L 15/42; A61L 15/60
See application file for complete search history.

(56) References Cited

U.S. PATENT DOCUMENTS 5,676,660 A * 10/1997 Mukaida .................. A61F 13/53
604/367
5,684,106 A 11/1997 Johnson et al.
(Continued)

FOREIGN PATENT DOCUMENTS

AU 682117 A 1/1996
CN 1845948 A 10/2006
(Continued)

OTHER PUBLICATIONS

Australian Patent Examination Report dated Dec. 8, 2015, issued in Australian patent application No. 2012359876. (4 pages).
(Continued)

*Primary Examiner* — Michele M Kidwell
(74) *Attorney, Agent, or Firm* — Westerman, Hattori, Daniels & Adrian, LLP

(57) ABSTRACT

To provide an absorbent article that has a high absorption speed, is unlikely to cause a liquid to remain on a skin-contacting surface, has excellent dry feeling, and is unlikely to cause excreted body fluid to return. The present invention provides an absorbent article comprising an absorber composed of at least one absorbent layer, wherein a water-absorbent resin powder meeting the following requirements (a) to (d) is disposed in an uppermost layer of the absorber: (a) a bulk density: 0.45 g/ml to 0.62 g/ml; (b) an absorption speed by a vortex method: 20 seconds to 50 seconds; (c) a liquid-passing speed under load: 10 seconds or less; and (d) a moisture absorption blocking ratio: 5% or less.

11 Claims, 3 Drawing Sheets

(51) Int. Cl.
*A61L 15/60* (2006.01)
*A61L 15/42* (2006.01)
*A61F 13/532* (2006.01)
*A61L 15/26* (2006.01)

(56) References Cited

U.S. PATENT DOCUMENTS

| | | | |
|---|---|---|---|
| 6,297,319 B1 * | 10/2001 | Nagasuna | A61L 15/60 525/141 |
| 7,473,470 B2 | 1/2009 | Ishizaki et al. | |
| 8,598,254 B2 | 12/2013 | Tada et al. | |
| 2006/0282052 A1 | 12/2006 | Saito et al. | |
| 2007/0066167 A1 | 3/2007 | Wada et al. | |
| 2007/0141338 A1 | 6/2007 | Ishizaki et al. | |
| 2008/0221229 A1 * | 9/2008 | Torii | A61F 13/53 521/56 |
| 2010/0121296 A1 | 5/2010 | Noda et al. | |
| 2010/0261850 A1 * | 10/2010 | Mitsukami | C08J 3/245 525/329.7 |
| 2011/0237739 A1 | 9/2011 | Tada et al. | |
| 2011/0313113 A1 | 12/2011 | Sakamoto et al. | |
| 2013/0026412 A1 | 1/2013 | Machida et al. | |
| 2013/0066019 A1 | 3/2013 | Okuda et al. | |
| 2013/0123435 A1 | 5/2013 | Okuda et al. | |

FOREIGN PATENT DOCUMENTS

| | | |
|---|---|---|
| EP | 0278601 A2 | 8/1988 |
| EP | 2399944 A1 | 12/2011 |
| EP | 2548910 A1 | 1/2013 |
| EP | 2557095 A1 | 2/2013 |
| JP | 09-276391 A | 10/1997 |
| JP | 2001-276124 A | 10/2001 |
| JP | 2003-082250 A | 3/2003 |
| JP | 2003-235889 A | 8/2003 |
| JP | 2004-275225 A | 10/2004 |
| JP | 2005-095759 A | 4/2005 |
| JP | 2006-116535 A | 5/2006 |
| JP | 2008-297512 A | 12/2008 |
| JP | 2009-51952 A | 3/2009 |
| JP | 2010-17536 A | 1/2010 |
| JP | 2010-059254 A | 3/2010 |
| JP | 2010-185029 A | 8/2010 |
| JP | 2011-019896 A | 2/2011 |
| JP | 2011-178969 A | 9/2011 |
| JP | 2011-224386 A | 11/2011 |
| WO | 95/33558 A1 | 5/1995 |
| WO | 2005/092955 A1 | 10/2005 |
| WO | 2008/117755 A1 | 10/2008 |
| WO | 2009/031701 A1 | 3/2009 |

OTHER PUBLICATIONS

Third party observation dated Jun. 5, 2015, submitted against the counterpart Japanese Patent Application No. 2011-285292 (12 pages).
Written Opinion dated Nov. 20, 2015, issued in counterpart Application No. 11201403651R. (5 pages).
Chinese Office Action dated Jan. 29, 2015, issued in corresponding CN Patent Application No. 201280064766.5 (8 pages).
Office Action dated Mar. 10, 2016, issued in counterpart Japanese Patent Application No. 2011-285292. (5 pages).
Singapore Search Report and Written Opinion dated Mar. 23, 2015, issued in corresponding SG Patent Application No. 11201403651R (7 pages).
Notification of Transmittal of Translation of the International Preliminary Report on Patentability (Forms PCT/IB/326) of International Application No. PCT/JP2102/008170 dated Jul. 10, 2014 with Forms PCT/IB/373 and PCT/ISA/237. (8 pages).
International Search Report for PCT/JP2012/008170, dated May 15, 2013.
Written Opinion for PCT/JP2012/008170 dated May 15, 2013.
Taiwanese Office Action dated Oct. 29, 2014, issued in Taiwanese Application No. 101149692. (5 pages).

* cited by examiner

[Fig. 1]
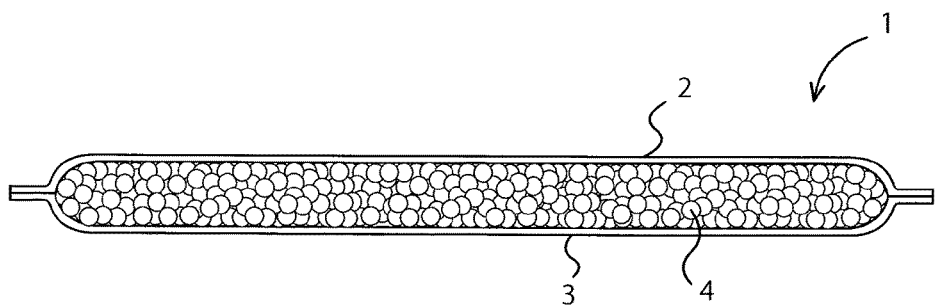
[Fig. 2]
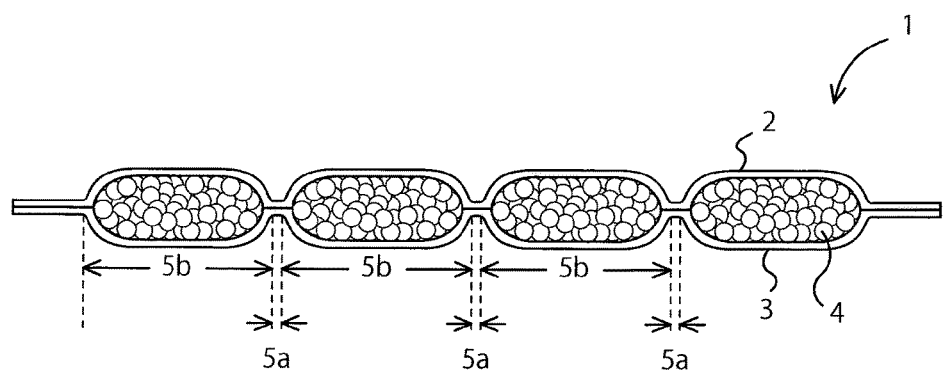
[Fig. 3]
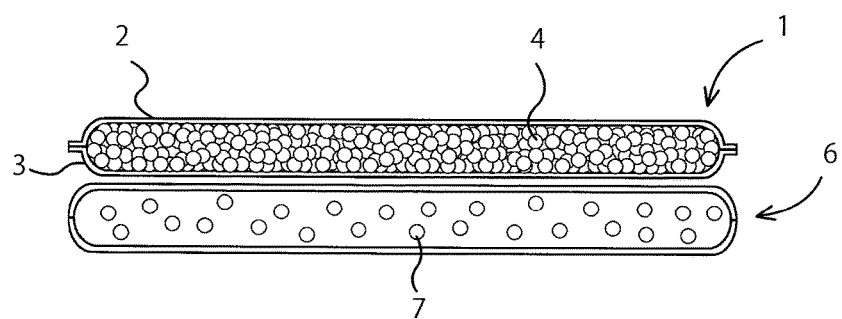

[Fig. 4]
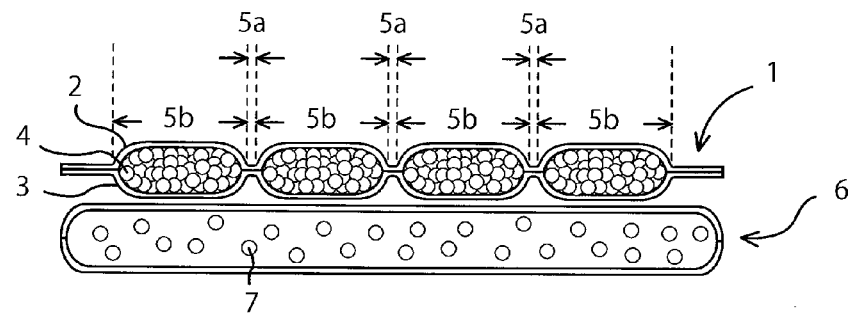
[Fig. 5]
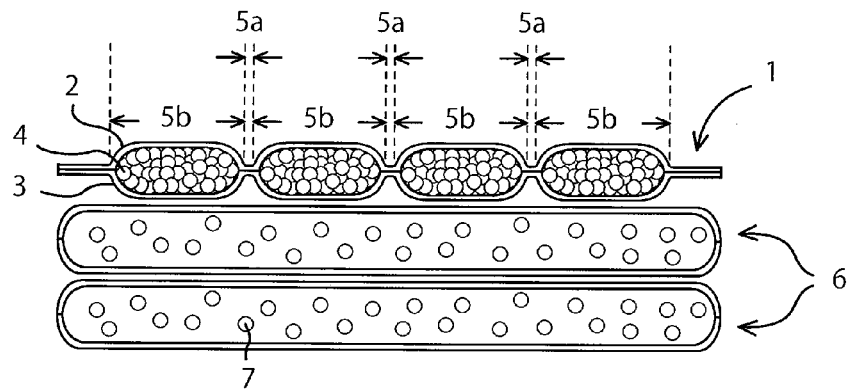
[Fig. 6]
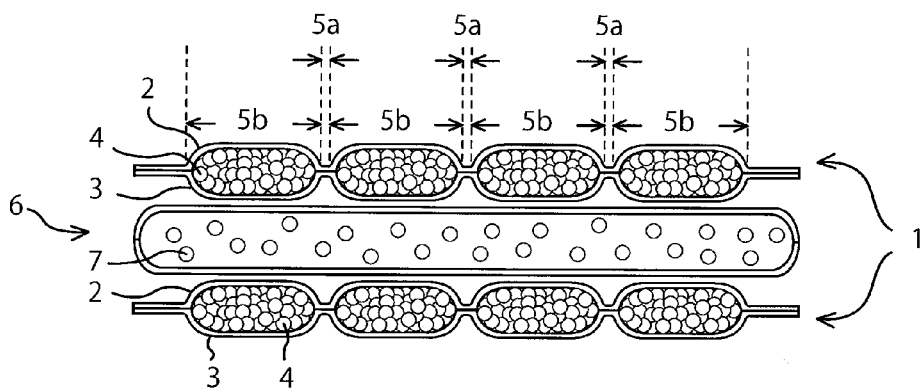

[Fig. 7]
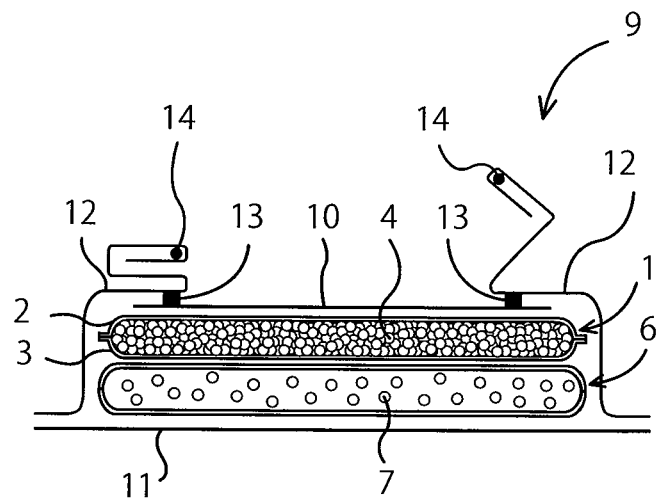
[Fig. 8]
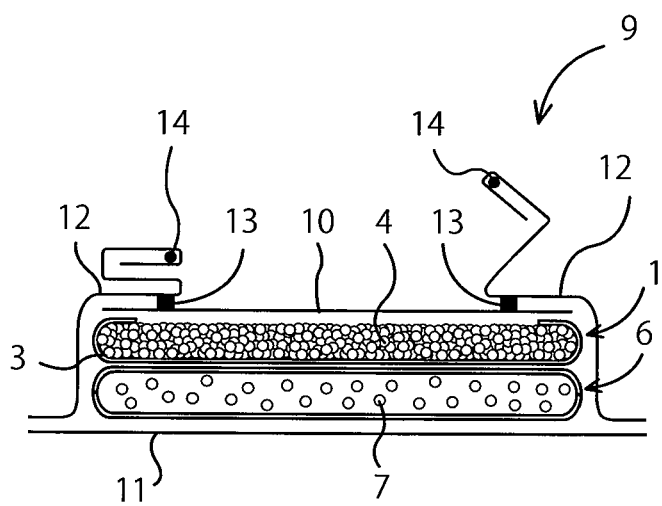

ABSORBENT ARTICLE CONTAINING A WATER-ABSORBENT RESIN POWDER

TECHNICAL FIELD

The present invention relates to an absorbent article, in particular, an improvement of the absorbing performance of an absorbent article such as a disposable diaper and a sanitary napkin.

BACKGROUND ART

An absorbent article such as a disposable diaper, a sanitary napkin, and an incontinence pad includes an absorber that absorbs and retains body fluid excreted from a body such as urine and menstrual blood, a flexible liquid-permeable top sheet disposed on a body-contacting side, and a liquid-non-permeable back sheet disposed on a side opposite to the body-contacting side. The absorber is generally composed of: a hydrophilic fibrous base material such as wood pulp; and a water-absorbent resin powder. Body fluid passes through the top sheet made of a nonwoven fabric or the like and is absorbed by the absorber. The absorbed body fluid is diffused by the fibrous base material such as wood pulp within the absorber, and absorbed and retained by the water-absorbent resin powder.

Patent Literatures 1 to 4 propose water-absorbent resin powders that can be used in absorbers. Patent Literature 1 discloses an absorbent resin particle that contains a crosslinked polymer (A1) containing a water-soluble vinyl monomer (a1) and/or a hydrolyzable vinyl monomer (a2) and a crosslinking agent (b) as essential constitutional units and in which a hydrophobic material (C) is present within the absorbent resin particle in an amount of 0.01 to 10.0% by weight with respect to the weight of the crosslinked polymer (A1) and a hydrophobic material (D) is present on the surface of the absorbent resin particle in an amount of 0.001 to 1.0% by weight with respect to the weight of the crosslinked polymer (A1).

Patent Literature 2 discloses a method for manufacturing a water-absorbent resin particle (D), the method including: a first step of conducting reversed-phase suspension polymerization of a water-soluble ethylenically unsaturated monomer solution containing a crosslinking agent, in a hydrophobic organic solvent in the presence of a dispersant to obtain a reaction mixture (A) containing a water-containing water-absorbent resin particle (a); a second step of further adding a water-soluble ethylenically unsaturated monomer solution containing a crosslinking agent to the (A) and conducting reversed-phase suspension polymerization to obtain a reaction mixture (B) containing a water-containing water-absorbent resin particle (b); a third step of dehydrating and desolvating the (B) to obtain a water-absorbent resin cake (C); and a fourth step of drying the water-absorbent resin cake, wherein the bulk density of the water-containing water-absorbent resin particle (b) is 0.25 to 0.35 g/ml and the bulk density of the water-absorbent resin particle (D) after drying is 0.45 to 0.55 g/ml.

Patent Literature 3 discloses an absorbent article that contains: a water-absorbent resin (i) whose gel liquid-passing rate (ml/min) is from 0.01 to 3; and a water-absorbent resin (ii) whose gel liquid-passing rate (ml/min) is from 5 to 200.

Patent Literature 4 discloses a water-absorbent resin composition characterized by containing a water-absorbent resin (A) and a modifier (B) whose surface tension is 10 to 30 dyne/cm and which has a binding group that can chemically bind to the water-absorbent resin (A).

Meanwhile, in order to make an absorbent article thin, reduction of the amount of the fibrous base material and increase of the amount of the water-absorbent resin powder in the absorber have been addressed. Such a thin absorber has a problem of so-called gel blocking. In other words, when an absorber in which the amount of the fibrous base material is reduced and the amount of the water-absorbent resin powder is increased absorbs body fluid, the water-absorbent resin powder on the skin-contacting side initially absorbs the body fluid and swells. However, since the content of the water-absorbent resin powder in the absorber is high, the swollen water-absorbent resin powders are likely to come into contact with each other. As a result, a void as a passage for body fluid is closed, and the absorber cannot exert a certain absorbing ability. This phenomenon is called gel blocking. The technologies for improving the gel blocking phenomenon are disclosed in Patent Literature 5 to 8.

Patent Literature 5 discloses an absorbent article that includes a liquid-permeable top sheet, a liquid-non-permeable back sheet, and a liquid-retentive absorber interposed between both sheets and is characterized in that the absorber meets the following conditions 1) and 1') and a high-water-absorbent polymer contained in the absorber meets the following conditions 2) and 3).

1) The absorber contains a fibrous base material and the high-water-absorbent polymer as principal components and 45 to 90% by weight of the total weight of the absorber is the high-water-absorbent polymer.

1') The absorber is composed of two or more layers, at least one of the layers is a layer made of the fibrous base material, at least of the other layers is a layer made of the high-water-absorbent polymer or a layer made of a mixture of the high-water-absorbent polymer and the fibrous base material, and the layer made of the fibrous base material is a sheet-shaped layer obtained by adhering fiberized and laminated pulp fibers by a binder.

2) The high-water-absorbent polymer is made of a crosslinked body particle having a high crosslinking density in a surface portion thereof, and its absorption amount of a saline by a centrifugal dehydration method is equal to or greater than 25 g/g.

3) When: a cylinder having a cross-sectional area of 4.91 $cm^2$ (an inner diameter: 25 mm phi) is filled with 0.5 g of the high-water-absorbent polymer and a saline; the high-water-absorbent polymer is swollen by the saline until reaching a saturated state; and 50 ml of the saline is passed through the cylinder after the swollen high-water-absorbent polymer sediments, a liquid-passing time is equal to or less than 20 seconds.

Patent Literature 6 discloses an absorbent article that includes a top sheet, a back sheet, and an absorber interposed between both sheets and containing a water-absorbent polymer and a fiber, and in which the absorber contains a water-absorbent polymer whose swollen gel has a repose angle equal to or less than 45 degrees, as the water-absorbent polymer, and has a water-absorbent polymer high concentration region where the content of the water-absorbent polymer exceeds a water-absorbent polymer average content calculated by the following equation.

Water-absorbent polymer average content (% by mass)=(total mass of all water-absorbent polymer contained in absorber/total mass of absorber)×100

Patent Literature 7 discloses a body fluid absorbent article that includes a back sheet, a liquid-permeable top sheet, and an absorber interposed between both sheets and composed of a pulp and a high-absorbent polymer and in which the ratio of the high-absorbent polymer to the total weight of the pulp and the high-absorbent polymer of the absorber is 30 to 60% by weight, and with regard to the high-absorbent polymer, in its polymer particle size distribution, particles with a size of 500 micrometers or greater are 10% by weight, particles with a size of 250 to 500 micrometers are 70% by weight, and particles with a size of 250 micrometers or less are 20% by weight, the degree of ununiformity of its polymer particle shape is 0.3 to 0.5 g/ml in bulk density evaluation, and its body fluid sucking/absorbing performance of shifting body fluid retained in a pulp fiber void toward the high-absorbent polymer side is equal to or greater than 5 g/g for 15 seconds from start of absorption.

Patent literature 8 discloses a disposable absorbent article comprising an absorbent mat between a liquid-permeable top sheet and a liquid-impermeable back sheet, the absorbent mat comprising, in the order recited from the top sheet side, a sheet-shaped water-absorbent layer that contains a water-absorbent resin powder but that does not contain pulp fibers; and a fiber assembly layer that contains a water-absorbent resin powder and pulp fibers; wherein the sheet-shaped water-absorbent layer includes a plurality of water-absorbent resin powder presence regions in each of which the water-absorbent resin powder is wrapped, a plurality of water-absorbent resin powder absence regions each being formed between the two adjacent water-absorbent resin powder presence regions.

CITATION LIST

Patent Literature

PTL 1: Japanese Patent Publication No. 2010-185029
PTL 2: Japanese Patent Publication No. 2010-59254
PTL 3: Japanese Patent Publication No. 2003-235889
PTL 4: Japanese Patent Publication No. 2003-82250
PTL 5: Japanese Patent No. 3722550
PTL 6: Japanese Patent Publication No. 2011-19896
PTL 7: Japanese Patent No. 3783914
PTL 8: Japanese Patent Publication No. 2004-275225

SUMMARY OF INVENTION

Technical Problem

The present invention has been made in view of the problem arising when making a thin absorbent article. In other words, an object of the present invention is to provide an absorbent article that has a high absorption speed, is unlikely to cause a liquid to remain on a skin-contacting surface, has excellent dry feeling, and is unlikely to cause excreted body fluid to return.

Solution to Problem

The present invention, which can solve the above problem, provides an absorbent article comprising an absorber composed of at least one absorbent layer, wherein a water-absorbent resin powder meeting the following requirements (a) to (d) is disposed in an uppermost layer of the absorber;
(a) a bulk density: 0.45 g/ml to 0.62 g/ml;
(b) an absorption speed by a vortex method: 20 seconds to 50 seconds;
(c) a liquid-passing speed under load: 10 seconds or less; and
(d) a moisture absorption blocking ratio: 5% or less.

Since the water-absorbent resin powder used in the present invention can readily pass body fluid to a lower portion of the absorber. As a result, the absorbent article of the present invention has a high absorption speed, excellent dry feeling of the absorber surface, and is unlikely to cause excreted body fluid to return. In addition, even when body fluid is repeatedly absorbed, the absorption speed is unlikely to decrease.

In light of exhibiting high water absorbability, an absorption ratio of the water-absorbent resin powder is preferably from 40 g/g to 55 g/g and a water-retaining capacity of the water-absorbent resin powder is preferably from 20 g/g to 45 g/g.

The water-absorbent resin powder is preferably, for example, a water-absorbent resin powder obtained by treating, with a surface modifier (B), a crosslinked polymer (A) obtained by polymerizing a monomer composition containing: a water-soluble ethylenically unsaturated monomer (a1) and/or a hydrolyzable monomer (a2) producing the water-soluble ethylenically unsaturated monomer (a1) by hydrolysis; and an internal crosslinking agent (b). An amount of the surface modifier (B) for the treatment is preferably 0.001 part by mass to 1 part by mass with respect to 100 parts by mass of the crosslinked polymer (A). The surface modifier (B) is preferably at least one member selected from the group consisting of amino-modified polysiloxanes, carboxy-modified polysiloxanes, and silica.

The uppermost layer of the absorber of the absorbent article of the present invention preferably has a plurality of water-absorbent resin powder present regions in which the water-absorbent resin powder is enveloped and a water-absorbent resin powder absent region adjacent to the water-absorbent resin powder present regions. The absorber of the absorbent article of the present invention preferably has an absorber comprising a water-absorbent resin powder and a fibrous base material as a lower layer adjacent to the uppermost layer.

Advantageous Effects of Invention

The absorbent article of the present invention has a high absorption speed, has excellent dry feeling, and is unlikely to cause excreted body fluid to return.

BRIEF DESCRIPTION OF DRAWINGS

FIG. 1 is a schematic cross-sectional view of a preferred embodiment of the absorber used in the present invention.
FIG. 2 is a schematic cross-sectional view of a preferred embodiment of the absorber used in the present invention.
FIG. 3 is a schematic cross-sectional view of a preferred embodiment of the absorber used in the present invention.
FIG. 4 is a schematic cross-sectional view of a preferred embodiment of the absorber used in the present invention.
FIG. 5 is a schematic cross-sectional view of a preferred embodiment of the absorber used in the present invention.
FIG. 6 is a schematic cross-sectional view of a preferred embodiment of the absorber used in the present invention.
FIG. 7 is a schematic cross-sectional view of a preferred embodiment of the absorbent article of the present invention.
FIG. 8 is a schematic cross-sectional view of another preferred embodiment of the absorbent article of the present invention.

DESCRIPTION OF EMBODIMENTS

The present invention is directed to an absorbent article comprising an absorber composed of at least one absorbent layer, wherein a water-absorbent resin powder meeting the following requirements (a) to (d) is disposed in an uppermost layer of the absorber;
(a) a bulk density: 0.45 g/ml to 0.62 g/ml;
(b) an absorption speed by a vortex method: 20 seconds to 50 seconds;
(c) a liquid-passing speed under load: 10 seconds or less; and
(d) a moisture absorption blocking ratio: 5% or less.

First, the water-absorbent resin powder used in the present invention will be described. The water-absorbent resin powder has (a) a bulk density in a range from 0.45 g/ml to 0.62 g/ml. The bulk density of the water-absorbent resin powder is preferably 0.50 g/ml or more, and more preferably 0.52 g/ml or more, and is preferably 0.61 g/ml or less, and more preferably 0.60 g/ml or less. The bulk density is an index of the shape of the water-absorbent resin powder. If the bulk density falls within the above range, a void is easily formed for a passage of body fluid between the water-absorbent resin powders. As a result, the absorption speed and repeated-absorption speed become favorable. The method for measuring the bulk density will be described later.

The water-absorbent resin powder of the present invention has (b) an absorption speed by the vortex method in a range from 20 seconds to 50 seconds. The absorption speed of the water-absorbent resin powder by the vortex method is preferably 22 seconds or more, and more preferably 25 seconds or more, and is preferably 48 seconds or less, and more preferably 45 seconds or less. If the absorption speed exceeds 50 seconds, the body fluid cannot be sufficiently absorbed when a large amount of body fluid is excreted at a high speed at one time. As a result, liquid leakage may occur. The absorption speed is more preferred if it is lower, but if the absorption speed is less than 20 seconds, the stability of the water-absorbent resin powder to urine, in particular, its stability to urine under load, may be lowered. The absorption speed by the vortex method is evaluated by measuring a time (seconds) taken to absorb body fluid. Thus, the shorter measured time (seconds) means the higher absorption speed.

The water-absorbent resin powder has (c) a liquid-passing speed under load of 10 seconds or less. The liquid-passing speed under load is preferably 8 seconds or less, and more preferably 5 seconds or less. If the liquid-passing speed under load exceeds 10 seconds, failure of diffusing body fluid is likely to occur within the absorber. Thus, liquid leakage may be likely to occur. The liquid-passing speed under load is evaluated by measuring a time (seconds) taken for a certain amount of liquid to pass through a water-absorbent resin powder that is previously made to absorb water to swell, in a state where a load is applied to the water-absorbent resin powder. Thus, the shorter measured time (seconds) means the higher absorption speed.

The water-absorbent resin powder has (d) a moisture absorption blocking ratio of 5% or less. The moisture absorption blocking ratio is more preferably 4% or less, and even more preferably 3% or less. If the moisture absorption blocking ratio exceeds 5%, the water-absorbent resin powder is likely to aggregate. Thus, when an absorber is manufactured, problems arise such as the water-absorbent resin powder being easily stuck in a feed pipe in a manufacturing machine or a manufacturing line, or the water-absorbent resin powder not being able to be uniformly applied to a nonwoven fabric. In addition, return of excreted body fluid may occur.

The water-absorbent resin powder of the present invention preferably has an absorption ratio of 40 g/g or more, more preferably 42 g/g or more, and even more preferably 44 g/g or more, and preferably has an absorption ratio of 55 g/g or less, more preferably 53 g/g or less, and even more preferably 51 g/g or less. The absorption ratio is a measure indicating how much water the water-absorbent resin powder can absorb. If the absorption ratio is less than 40 g/g, a large amount of the water-absorbent resin powder has to be used in order to maintain an absorption capacity at a predetermined level, and thus it is difficult to manufacture a thin absorber. In light of prevention of liquid leakage, the absorption ratio is more preferred if it is greater, but the absorption ratio is more preferably 55 g/g or less. This is because if the absorption ratio exceeds 55 g/g, the stability of the water-absorbent resin powder to urine tends to decrease.

The water-absorbent resin powder preferably has a water-retaining capacity of 20 g/g or more, more preferably 22 g/g or more, and even more preferably 24 g/g or more, and preferably has a water-retaining capacity of 45 g/g or less, more preferably 43 g/g or less, and even more preferably 40 g/g or less. The water-retaining capacity is a measure indicating how much absorbed liquid the water-absorbent resin powder can retain. If the water-retaining capacity is less than 20 g/g, a large amount of the water-absorbent resin powder has to be used in order to maintain a body fluid-retaining capacity at a predetermined level, and thus it may be difficult to manufacture a thin absorber. In light of prevention of liquid leakage, the water-retaining capacity is more preferred if it is greater, but the water-retaining capacity is more preferably 45 g/g or less. This is because if the water-retaining capacity exceeds 45 g/g, the stability of the water-absorbent resin powder to urine tends to decrease.

The bulk density, the absorption speed by the vortex method, the liquid-passing speed under load, the absorption ratio, and the water-retaining capacity of the water-absorbent resin powder can be adjusted by, for example, appropriately selecting a composition of a crosslinked polymer, a type of a surface modifier, the particle size of the water-absorbent resin powder, a drying condition, and the like.

The water-absorbent resin powder is preferably obtained by treating the surface of a crosslinked polymer (A) with a surface modifier (B). The crosslinked polymer (A) is preferably obtained by polymerizing a monomer composition containing a water-soluble ethylenically unsaturated monomer (a1) and/or a hydrolyzable monomer (a2) producing the water-soluble ethylenically unsaturated monomer (a1) by hydrolysis; and an internal crosslinking agent (b) as essential components.

The crosslinked polymer (A) will be described. The water-soluble ethylenically unsaturated monomer (a1) is not particularly limited, but a monomer having at least one water-soluble substituent and an ethylenically unsaturated group, or the like can be used. The water-soluble monomer means a monomer having a property of being dissolved at least in an amount of 100 g in 100 g of water at 25 degrees centigrade. In addition, the hydrolyzable monomer (a2) is hydrolyzed with water at 50 degrees centigrade, by the action of a catalyst (an acid, a base, or the like) where necessary, to produce the water-soluble ethylenically unsaturated monomer (a1). The hydrolysis of the hydrolyzable monomer (a2) may be conducted during or after the polymerization of the crosslinked polymer (A) or both during and after the polymerization of the crosslinked polymer (A). However, the hydrolysis of the hydrolyzable monomer (a2) is preferably conducted after the polymerization of the crosslinked polymer (A) in light of the molecular weight of the obtained water-absorbent resin powder and the like.

Examples of the water-soluble substituent include a carboxyl group, a sulfo group, a sulfoxy group, a phosphono group, a hydroxyl group, a carbamoyl group, an amino group, or salts thereof and an ammonium salt. A salt of a carboxyl group (a carboxylate), a salt of a sulfo group (a sulfonate), and an ammonium salt are preferred. In addition, examples of the salts include salts of alkali metal such as lithium, sodium, and potassium and salts of alkaline earth metal such as magnesium and calcium. The ammonium salt may be any of salts of primary to tertiary amines or a quaternary ammonium salt. Among these salts, in light of absorption properties, alkali metal salts and ammonium salts are preferred, and alkali metal salts are more preferred, and sodium salts are further preferred.

As the water-soluble ethylenically unsaturated monomer having a carboxyl group and/or a salt thereof, an unsaturated carboxylic acid having 3 to 30 carbon atoms and/or a salt thereof are preferred. Specific examples of the water-soluble ethylenically unsaturated monomer having a carboxyl group and/or a salt thereof include unsaturated monocarboxylic acids and/or salts thereof such as (meth)acrylic acid, (meth)acrylic acid salt, crotonic acid, and cinnamic acid; unsaturated dicarboxylic acids and/or salts thereof such as maleic acid, maleate, fumaric acid, citraconic acid, and itaconic acid; and monoalkyl (1 to 8 carbon atoms) esters of unsaturated dicarboxylic acids and/or salts thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that in the description of the present invention, "(meth)acrylic" means "acrylic" and/or "methacrylic".

As a water-soluble ethylenically unsaturated monomer having a sulfo group and/or a salt thereof, a sulfonic acid having 2 to 30 carbon atoms and/or a slat thereof are preferred. Specific examples of the water-soluble ethylenically unsaturated monomer having a sulfo group and/or a salt thereof include aliphatic or aromatic vinyl sulfonic acids such as vinyl sulfonic acid, (meth)allyl sulfonic acid, styrene sulfonic acid, and alpha-methyl styrene sulfonic acid; (meth) acryloyl-containing alkyl sulfonic acids such as (meth) acryloxy propyl sulfonic acid, 2-hydroxy-3-(meth)acryloxy propyl sulfonic acid, 2-(meth)acryloylamino-2,2-dimethylethane sulfonic acid, 3-(meth)acryloxyethane sulfonic acid, 2-(meth)acrylamide-2-methylpropane sulfonic acid, and 3-(meth)acrylamide-2-hydroxypropane sulfonic acid; and alkyl(meth)allyl sulfosuccinate.

Examples of a water-soluble ethylenically unsaturated monomer having a sulfoxy group and/or a salt thereof include sulfate ester of hydroxyalkyl (meth)acrylate; and sulfate ester of polyoxyalkylene mono(meth)acrylate.

Examples of a water-soluble ethylenically unsaturated monomer having a phosphono group and/or a salt thereof include phosphate monoesters of (meth)acrylic acid hydroxyalkyl, phosphate diesters of (meth)acrylic acid hydroxyalkyl, and (meth)acrylic acid alkylphosphonic acids.

Examples of a water-soluble ethylenically unsaturated monomer having a hydroxyl group include mono-ethylenically unsaturated alcohols having 3 to 15 carbon atoms such as (meth)allyl alcohol and (meth)propenyl alcohol; mono-ethylenically unsaturated carboxylates or mono-ethylenically unsaturated ethers of bivalent to hexavalent polyols such as alkylene glycol having 2 to 20 carbon atoms, glycerin, sorbitan, diglycerin, pentaerythritol, and polyalkylene (2 to 4 carbon atoms) glycol (weight average molecular weight: 100 to 2000). Specific examples of them include hydroxyethyl(meth)acrylate, hydroxypropyl(meth)acrylate, triethyleneglycol(meth)acrylate, and poly-oxyethylene-oxypropylene mono(meth)allyl ether.

Examples of a water-soluble ethylenically unsaturated monomer having a carbamoyl group include (meth)acrylamide; N-alkyl (1 to 8 carbon atoms) (meth)acrylamides such as N-methyl acrylamide; N,N-dialkyl (alkyl having 1 to 8 carbon atoms) acrylamides such as N,N-dimethyl acrylamide and N,N-di-n- or i-propyl acrylamide; N-hydroxyalkyl (1 to 8 carbon atoms) (meth)acrylamides such as N-methylol (meth)acrylamide and N-hydroxyethyl (meth) acrylamide; and N,N-dihydroxyalkyl (1 to 8 carbon atoms) (meth)acrylamides such as N,N-dihydroxyethyl (meth)acrylamide. As an unsaturated monomer having a group composed of an amide, in addition to them, vinyl lactams having 5 to 10 carbon atoms (N-vinyl pyrrolidone, etc.) and the like can also be used.

Examples of a water-soluble ethylenically unsaturated monomer having an amino group include an amino group-containing ester of a mono-ethylenically unsaturated mono- or di-carboxylic acid and an amino group-containing amide of a mono-ethylenically unsaturated mono- or di-carboxylic acid. As the amino group-containing ester of a mono-ethylenically unsaturated mono- or di-carboxylic acid, dialkylaminoalkyl(meth)acrylate, di(hydroxyalkyl)aminoalkyl ester, morpholinoalkyl ester, and the like can be used, and examples thereof include dimethylaminoethyl (meth) acrylate, diethylamino (meth)acrylate, morpholinoethyl (meth)acrylate, dimethylaminoethyl fumarate, and dimethylaminoethyl malate. As the amino group-containing amide of a mono-ethylenically unsaturated mono- or di-carboxylic acid, monoalkyl (meth)acrylamide is preferred, and examples thereof include dimethylaminoethyl (meth)acrylamide and diethylaminoethyl (meth)acrylamide. As the water-soluble ethylenically unsaturated monomer having an amino group, in addition to them, vinylpyridines such as 4-vinylpyridine and 2-vinylpyridine can also be used.

The hydrolyzable monomer (a2) producing the water-soluble ethylenically unsaturated monomer (a1) by hydrolysis is not particularly limited, but an ethylenically unsaturated monomer having at least one hydrolyzable substituent that becomes a water-soluble substituent by hydrolysis is preferred. Examples of the hydrolyzable substituent include a group containing an acid anhydride, a group containing an ester linkage, and a cyano group.

As an ethylenically unsaturated monomer having a group containing an acid anhydride, an unsaturated dicarboxylic anhydride having 4 to 20 carbon atoms is used, and examples thereof include maleic anhydride, itaconic anhydride, and citraconic anhydride. Examples of an ethylenically unsaturated monomer having a group containing an ester linkage include lower alkyl esters of mono-ethylenically unsaturated carboxylic acids such as methyl (meth) acrylate and ethyl (meth)acrylate; and esters of mono-ethylenically unsaturated alcohols such as vinyl acetate and (meth)allyl acetate. Examples of an ethylenically unsaturated monomer having a cyano group include vinyl group-containing nitrile compounds having 3 to 6 carbon atoms such as (meth)acrylonitrile and 5-hexenenitrile.

As the water-soluble ethylenically unsaturated monomer (a1) and the hydrolyzable monomer (a2), those described in Japanese Patent No. 3648553, Japanese Patent Publication No. 2003-165883, Japanese Patent Publication No. 2005-75982, and Japanese Patent Publication No. 2005-95759 can be further used.

As each of the water-soluble ethylenically unsaturated monomer (a1) and the hydrolyzable monomer (a2), a single monomer or a mixture of two or more monomers may be used. The same applies to the case where the water-soluble ethylenically unsaturated monomer (a1) and the hydrolyzable monomer (a2) are used in combination. In addition, when the water-soluble ethylenically unsaturated monomer (a1) and the hydrolyzable monomer (a2) are used in combination, the molar content ratio (a1/a2) of them is preferably from 75/25 to 99/1, more preferably from 85/15 to 95/5, even more preferably from 90/10 to 93/7, and most preferably from 91/9 to 92/8. When the molar content ratio falls within the above range, the absorbing performance becomes further preferable.

As the monomer constituting the crosslinked polymer (A), in addition to the water-soluble ethylenically unsaturated monomer (a1) and the hydrolyzable monomer (a2), another vinyl monomer (a3) that is copolymerizable with these monomers can be used. As the copolymerizable other vinyl monomer (a3), hydrophobic vinyl monomers and the like can be used, but it is not limited to them. As the other vinyl monomer (a3), the following vinyl monomers (i) to (iii) and the like are used.

(i) Aromatic Ethylenically Unsaturated Monomers Having 8 to 30 Carbon Atoms;

Styrenes such as styrene, alpha-methylstyrene, vinyltoluene, and hydroxystyrene; vinylnaphthalene; and halogen substitutions of styrene such as dichlorostyrene.

(ii) Aliphatic Ethylenically Unsaturated Monomers Having 2 to 20 Carbon Atoms;

Alkenes such as ethylene, propylene, butene, isobutylene, pentene, heptene, di-isobutylene, octene, dodecene, and octadecene; and alkadienes such as butadiene, and isoprene.

(iii) Alicyclic Ethylenically Unsaturated Monomers Having 5 to 15 Carbon Atoms;

Mono-ethylenically unsaturated monomers such as pinene, limonene, and indene; and polyethylenic vinyl-polymerizable monomers such as cyclopentadiene, bicyclopentadiene, and ethylidene norbornene.

As the other vinyl monomer (a3), those described in Japanese Patent No. 3648553, Japanese Publication No. 2003-165883, Japanese Patent Publication No. 2005-75982, and Japanese Patent Publication No. 2005-95759 can be further used.

When the other vinyl monomer (a3) is used, the content (mole %) of the other vinyl monomer (a3) with respect to the total amount (100 mole %) of the water-soluble ethylenically unsaturated monomer (a1) and the hydrolyzable monomer (a2) is preferably 0.01 mole % to 5 mole %, more preferably 0.05 mole % to 3 mole %, even more preferably 0.08 mole % to 2 mole %, and most preferably 0.1 mole % to 1.5 mole %. It is noted that in light of absorption properties, the content of the other vinyl monomer (a3) is most preferably 0 mole %.

Examples of the internal crosslinking agent (b) can include an internal crosslinking agent (b1) having two or more ethylenically unsaturated groups, an internal crosslinking agent (b2) having: at least one functional group that can react with a water-soluble substituent of the water-soluble ethylenically unsaturated monomer (a1) and/or a water-soluble substituent produced by hydrolysis of the hydrolyzable monomer (a2); and at least one ethylenically unsaturated group, and an internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2).

Examples of the internal crosslinking agent (b1) having two or more ethylenically unsaturated groups include bis (meth)acrylamides having 8 to 12 carbon atoms, poly(meth) acrylates of polyols having 2 to 10 carbon atoms, polyallylamines having 2 to 10 carbon atoms, and poly(meth)allyl ethers of polyols having 2 to 10 carbon atoms. Specific examples of them include N,N'-methylene bis(meth)acrylamide, ethylene glycol di(meth)acrylate, poly (polymerization degree of 2 to 5) ethylene glycol di(meth)acrylate, propylene glycol di(meth)acrylate, glycerol (di or tri)acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth) acrylate.

Examples of the internal crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group include ethylenically unsaturated compounds having 6 to 8 carbon atoms and an epoxy group, ethylenically unsaturated compounds having 4 to 8 carbon atoms and a hydroxyl group, and ethylenically unsaturated compounds having 4 to 8 carbon atoms and an isocyanato group. Specific examples of them include glycidyl (meth)acrylate, N-methylol (meth)acrylamide, hydroxyethyl (meth)acrylate, and isocyanato ethyl (meth) acrylate.

Examples of the internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2) can include polyhydric alcohols, polyvalent glycidyls, polyvalent amines, polyvalent aziridines, and polyvalent isocyanates. Examples of polyvalent glycidyl compounds include ethylene glycol diglycidyl ether and glycerin diglycidyl ether. Examples of polyvalent amine compounds include ethylenediamine, diethylenetriamine, triethylenetetramine, tetraethylenepentamine, pentaethylenehexamine, and polyethyleneimine. Examples of polyvalent aziridine compounds include Chemitite PZ-33 {2,2-bishydroxymethylbutanol-tris(3-(1-aziridinyl)propionate)}, Chemitite HZ-22 {1,6-hexamethylenediethyleneurea}, and Chemitite DZ-22 {diphenylmethane-bis-4,4'-N,N'-diethyleneurea}, available from Nippon Shokubai Co., Ltd. Examples of polyvalent polyisocyanate compounds include 2,4-tolylene diisocyanate and hexamethylene diisocyanate. These internal crosslinking agents may be used singly or two or more of them may be used in combination.

As the internal crosslinking agent (b), in light of absorbing performance (in particular, an absorption amount, an absorption speed, etc.), the internal crosslinking agent (b1) having two or more ethylenically unsaturated groups is preferred, poly(meth)allyl ethers of polyols having 2 to 10 carbon atoms are more preferred, triallylcyanurate, triallylisocyanurate, tetraallyloxyethane, or pentaerythritol triallyl ether is further preferred, and pentaerythritol triallyl ether is most preferred.

As the internal crosslinking agent (b), those described in Japanese Patent No. 3648553, Japanese Patent Publication No. 2003-165883, Japanese Patent Publication No. 2005-75982, and Japanese Patent Publication No. 2005-95759 can be further used.

The content (mole %) of the internal crosslinking agent (b) with respect to the total amount (100 mole %) of the water-soluble ethylenically unsaturated monomer (a1) and the hydrolyzable monomer (a2) is preferably from 0.001 mole % to 5 mole %, more preferably from 0.005 mole % to 3 mole %, and even more preferably from 0.01 mole % to 1 mole %. When the content falls within this range, the absorbing performance (in particular, an absorption amount, an absorption speed, etc.) becomes further favorable.

As the method for polymerizing the crosslinked polymer (A), a conventionally known method and the like can be used, and a solution polymerization method, an emulsion polymerization method, a suspension polymerization method, and a reversed-phase suspension polymerization method can be used. In addition, a polymerization liquid at the polymerization may be in the form of a thin film, mist, or the like. As the method for controlling the polymerization, an adiabatic polymerization method, a temperature-controlled polymerization method, an isothermal polymerization method, and the like can be used.

When the suspension polymerization method or the reversed-phase suspension polymerization method is employed as the polymerization method, conventionally known dispersants such as sucrose esters, phosphates, and sorbitan esters, protective colloids such as poval, alpha-olefin-maleic anhydride copolymers, and oxidized polyethylene, and the like can be used where necessary. In addition, in the case with the reversed-phase suspension polymerization method, polymerization can be conducted by using a solvent such as cyclohexane, normal hexane, normal heptane, toluene, and xylene. As the polymerization method, the solution polymerization method is preferred, and an aqueous solution polymerization method is more preferred since an organic solvent and the like are not used and it is advantageous in terms of production cost.

A water-containing gel {consisting of the crosslinked polymer and water} obtained by the polymerization can be chopped where necessary. The size (largest diameter) of the chopped gel is preferably from 50 micrometers to 10 cm, more preferably from 100 micrometers to 2 cm, and even more preferably from 1 mm to 1 cm. If the size falls within this range, dryability at a drying process becomes further favorable.

The chopping can be conducted by a known method, and can be conducted, for example, by using a conventional chopping apparatus such as a Bexmill, a rubber chopper, a Pharma Mill, a mincing machine, an impact type mill, and a roll type mill.

When a solvent (an organic solvent, water, etc.) is used for the polymerization, it is preferred to remove the solvent by distillation after the polymerization. When the solvent contains an organic solvent, the content (mass %) of the organic solvent with respect to the mass (100 mass %) of the crosslinked polymer after the removal by distillation is preferably from 0 mass % to 10 mass %, more preferably from 0 mass % to 5 mass %, even more preferably from 0 mass % to 3 mass %, and most preferably from 0 mass % to 1 mass %. When the content of the organic solvent falls within the above range, the absorbing performance (in particular, water-retaining capacity) of the water-absorbent resin powder becomes further favorable.

When the solvent contains water, the water content (mass %) with respect to the mass (100 mass %) of the crosslinked polymer after the removal by distillation is preferably from 0 mass % to 20 mass %, more preferably from 1 mass % to 10 mass %, even more preferably from 2 mass % to 9 mass %, and most preferably from 3 mass % to 8 mass %. When the water content (% by mass) falls within the above range, the absorbing performance and the breakability of the water-absorbent resin powder after drying become further favorable.

It is noted that the content of the organic solvent and the water content are obtained based on a decrease in the mass of a measurement sample from before heating to after heating by an infrared moisture measuring instrument {JE400 manufactured by Kett Electric Laboratory or the like: 120 plus or minus 5 degrees centigrade, 30 minutes, an atmospheric humidity before heating of 50 plus or minus 10% RH, lamp specifications of 100 V and 40 W}.

As the method for removing the solvent (including water) by distillation, a method in which removal by distillation (drying) is conducted by hot air at a temperature in a range from 80 degrees centigrade to 230 degrees centigrade, a thin film drying method with a drum dryer or the like heated at the temperature in a range from 100 degrees centigrade to 230 degrees centigrade, a (heating) reduced-pressure drying method, a freeze-drying method, a drying method with infrared rays, decantation, filtration, and the like can be used.

The crosslinked polymer (A) can be pulverized after being dried. The pulverizing method is not particularly limited, and, for example, an ordinary pulverizing apparatus such as a hammer type pulverizer, an impact type pulverizer, a roll type pulverizer, and a jet streaming type pulverizer can be used. The particle size of the pulverized crosslinked polymer (A) can be adjusted by sieving or the like where necessary.

The weight average particle size (micrometer) of the crosslinked polymer (A) that is sieved where necessary is preferably from 100 micrometers to 800 micrometers, more preferably from 200 micrometers to 700 micrometers, even more preferably from 250 micrometers to 600 micrometers, particularly preferably from 300 micrometers, to 500 micrometers, and most preferably from 350 micrometers to 450 micrometers. When the weight average particle size (micrometer) of the crosslinked polymer (A) falls within the above range, the absorbing performance becomes further favorable.

It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21). In other words, as JIS standard sieves, for example, sieves of 1000 micrometers, 850 micrometers, 710 micrometers, 500 micrometers, 425 micrometers, 355 micrometers, 250 micrometers, 150 micrometers, 125 micrometers, 75 micrometers, and 45 micrometers, and a tray are combined in order from above. About 50 g of a measurement particle is placed into the uppermost sieve, and shaken with the ro-tap test sieve shaker for 5 minutes. The weights of the measurement particles on each sieve and the tray are measured, and the weight fraction of the particles on each sieve is obtained with the total weight regarded as 100% by weight. The values are plotted in a log probability paper {the horizontal axis is used for the opening of the sieve (particle size) and the vertical axis is used for the weight fraction}, then a line is drawn so as to connect each point, and a particle size corresponding to 50% by weight of the weight fraction is obtained and regarded as a weight average particle size.

In addition, the lower the content of fine particles is, the more favorable the absorbing performance becomes. Thus, the content of fine particles having a size of 106 micrometers or less (preferably, 150 micrometers or less) in the entire particles is preferably 3 weight % or less, and even more preferably 1 weight % or less. The content of fine particles can be obtained by using the plot created when the above weight average particle size is obtained.

The crosslinked polymer (A) may be one polymer or a mixture of two or more polymers.

Examples of the surface modifier (B) include polyvalent metal compounds such as aluminum sulfate, potassium alum, ammonium alum, sodium alum, (poly) aluminum chloride, and hydrates thereof; polycation compounds such as polyethyleneimine, polyvinylamine, and polyallylamine; inorganic fine particles; a surface modifier (B1) containing a hydrocarbon group; a surface modifier (B2) containing a hydrocarbon group having a fluorine atom; and a surface modifier (B3) having a polysiloxane structure.

Examples of the inorganic fine particles include oxides such as silicon oxide, aluminum oxide, iron oxide, titanium oxide, magnesium oxide, and zirconium oxide, carbides such as silicon carbide and aluminum carbide, nitrides such as titanium nitride, and complexes thereof (e.g., zeolite, talc, etc.). Among them, oxides are preferred, and silicon oxide is further preferred. The volume average particle size of the inorganic fine particles is preferably from 10 nm to 5000 nm, more preferably from 30 nm to 1000 nm, even more preferably from 50 nm to 750 nm, and most preferably from 90 nm to 500 nm. It is noted that the volume average particle size is measured in a solvent by a dynamic light scattering method. Specifically, the volume average particle size is measured in cyclohexane as a solvent at a temperature of 25 degrees centigrade by using the nano track particle size distribution measuring instrument UPA-EX150 (light source: He—Ne laser) manufactured by Nikkiso Co., Ltd.

The specific surface area of the inorganic fine particles is preferably from 20 $m^2/g$ to 400 $m^2/g$, more preferably from 30 $m^2/g$ to 350 $m^2/g$, and even more preferably from 40 $m^2/g$ to 300 $m^2/g$. If the specific surface area falls within this range, the absorbing performance becomes further favorable. It is noted that the specific surface area is measured according to JIS Z8830:2001 (nitrogen, a volume method, a multipoint method).

The inorganic fine particles are commercially easily available. Examples thereof {hereinafter, trade name (chemical composition, volume average particle size nm, specific surface area $m^2/g$)} include Aerosil 130 (silicon dioxide, 16, 130), Aerosil 200 (silicon dioxide, 12, 200), Aerosil 300 (silicon dioxide, 7, 300), Aerosil MOX80 (silicon dioxide, 30, 80), Aerosil COK84 (silicon dioxide, 12, 170), Aerosil OX50T (silicon dioxide, 7, 40), titanium oxide P25 (titanium oxide, 20, 30), and Aluminum Oxide C (aluminum oxide, 13, 100) {Nippon Aerosil Co., Ltd.}; Denka Fused Silica F-300 (silicon dioxide, 11, 160) {Denki Kagaku Kogyo Kabushiki Kaisha}; Microd 850 (silicon dioxide, 13, 150) {Tokai Chemical Industry Co., Ltd.}; Amorphous Silica SP-1 (silicon dioxide, 14, 45) {Nozawa Corporation}; Syloid 622 (silicon dioxide, 17, 350) and Syloid ED50 (silicon dioxide, 8, 400) {Grace Japan Co., Ltd.}; Admafine SO-C1 (complex oxide, 0.1, 20) {Admatechs Company Limited}; Aerosil 200 (silicon dioxide, 100, 12) {Degussa AG: Germany}; Tokusil (silicon dioxide, 2.5, 120) and Reolosil (silicon dioxide, 2.5, 110) {Tokuyama Corporation}; Nipsil E220A (silicon dioxide, 2.5, 130) {Nihon Silica Kogyo K.K.}; and Klebosol 30CAL25 (silicon oxide, 12, 200) {Clariant (Japan) K.K.}.

Examples of the surface modifier (B1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, and mixtures of two or more of them.

Examples of polyolefin resins include a polymer that is obtained by polymerizing an olefin having 2 to 4 carbon atoms such as ethylene, propylene, isobutylene, and isoprene and has a weight average molecular weight from 1,000 to 1,000,000. The content of the olefin component in the polymer is preferably at least 50 mass % in 100% by mass of the polyolefin resin. Specific examples of polyolefin resins include polyethylene, polypropylene, polyisobutylene, poly(ethylene-isobutylene), and isoprene.

As a polyolefin resin derivative, a polymer that has a weight average molecular weight of 1,000 to 1,000,000 and in which a carboxy group (—COOH), 1,3-oxo-2-oxapropylene (—COOCO—), or the like is introduced into a polyolefin resin is preferred. Specific examples thereof include polyethylene thermal degradation products, polypropylene thermal degradation products, maleic acid-modified polyethylene, chlorinated polyethylene, maleic acid-modified polypropylene, ethylene-acrylic acid copolymers, ethylene-maleic anhydride copolymers, isobutylene-maleic anhydride copolymers, maleinated polybutadiene, ethylene-vinyl acetate copolymers, and maleinated products of ethylene-vinyl acetate copolymers.

As a polystyrene resin, a polymer having a weight average molecular weight of 1,000 to 1,000,000 and the like can be used.

As a polystyrene resin derivative, a polymer that contains styrene as an essential constituent monomer and has a weight average molecular weight of 1,000 to 1,000,000 is preferred. The content of styrene is preferably at least 50 mass % in 100 mass % of the polystyrene derivative. Specific examples of polystyrene resin derivatives include styrene-maleic anhydride copolymers, styrene-butadiene copolymers, and styrene-isobutylene copolymers.

Examples of waxes include waxes having a melting point of 50 degrees centigrade to 200 degrees centigrade such as paraffin wax, bees wax, carnauba wax, and beef tallow.

As a long-chain fatty acid ester, an ester of a fatty acid having 8 to 30 carbon atoms and an alcohol having 1 to 12 carbon atoms is preferred. Specific examples of long-chain fatty acid esters include methyl laurate, ethyl laurate, methyl stearate, ethyl stearate, methyl oleate, ethyl oleate, glycerin laurate monoester, glycerin stearate monoester, glycerin oleate monoester, pentaerythritol laurate monoester, pentaerythritol stearate monoester, pentaerythritol oleate monoester, sorbitol laurate monoester, sorbitol stearate monoester, sorbitol oleate monoester, sucrose palmitate monoester, sucrose palmitate diester, sucrose palmitate triester, sucrose stearate monoester, sucrose stearate diester, sucrose stearate triester, and beef tallow. Among them, in light of leakage resistance of the absorbent article, sucrose stearate monoester, sucrose stearate diester, and sucrose stearate triester are preferred, and sucrose stearate monoester and sucrose stearate diester are further preferred.

As a long-chain fatty acid and a salt thereof, a fatty acid having 8 to 30 carbon atoms and a salt thereof are preferred. Examples of fatty acids having 8 to 30 carbon atoms include lauric acid, palmitic acid, stearic acid, oleic acid, dimer acid, and behenic acid. As a metal component of a salt of the fatty acid having 8 to 30 carbon atoms, for example, zinc, calcium, magnesium, or aluminum (hereinafter, they are abbreviated as Zn, Ca, Mg, and Al) is preferred. Specific examples of salts of fatty acids having 8 to 30 carbon atoms include Ca palmitate, Al palmitate, Ca stearate, Mg stearate, and Al stearate. In light of leakage resistance of the absorbent article, as the long-chain fatty acid and a salt thereof, Zn stearate, Ca stearate, Mg stearate, and Al stearate are preferred, and Mg stearate is more preferred.

Examples of long-chain aliphatic alcohols include aliphatic alcohols having 8 to 30 carbon atoms such as lauryl alcohol, palmityl alcohol, stearyl alcohol, and oleyl alcohol. In light of leakage resistance of the absorbent article, as the long-chain aliphatic alcohol, palmityl alcohol, stearyl alcohol, and oleyl alcohol are preferred, and stearyl alcohol is further preferred.

Examples of the surface modifier (B2) containing a hydrocarbon group having a fluorine atom include perfluoroalkanes, perfluoroalkenes, perfluoroaryls, perfluoroalkyl ethers, perfluoroalkylcarboxylic acids or salts thereof, perfluoroalkyl alcohols, and mixtures of two or more of them.

As a perfluoroalkane, an alkane having 4 to 42 fluorine atoms and 1 to 20 carbon atoms is preferred. Examples of perfluoroalkanes include trifluoromethane, pentafluoroethane, pentafluoropropane, heptafluoropropane, heptafluorobutane, nonafluorohexane, tridecafluorooctane, and heptadecafluorododecane.

As a perfluoroalkene, an alkene having 4 to 42 fluorine atoms and 2 to 20 carbon atoms is preferred. Examples of perfluoroalkenes include trifluoroethylene, pentafluoropropene, trifluoropropene, heptafluorobutene, nonafluorohexene, tridecafluorooctene, and heptadecafluorododecene.

As a perfluoroaryl, an aryl having 4 to 42 fluorine atoms and 6 to 20 carbon atoms is preferred. Examples of perfluoroaryls include trifluorobenzene, pentafluorotoluene, trifluoronaphthalene, heptafluorobenzene, nonafluoroxylene, tridecafluorooctylbenzene, and heptadecafluorododecylbenzene.

As a perfluoroalkyl ether, an ether having 2 to 82 fluorine atoms and 2 to 40 carbon atoms is preferred. Examples of perfluoroalkyl ethers include ditrifluoromethyl ether, dipentafluoroethyl ether, dipentafluoropropyl ether, diheptafluoropropyl ether, diheptafluorobutyl ether, dinonafluorohexyl ether, ditridecafluorooctyl ether, and diheptadecafluorododecyl ether.

As a perfluoroalkylcarboxylic acid or a salt thereof, a carboxylic acid having 3 to 41 fluorine atoms and 1 to 21 carbon atoms or a salt thereof is preferred. Examples of perfluoroalkylcarboxylic acids or salts thereof include pentafluoroethanoic acid, pentafluoropropanoic acid, heptafluoropropanoic acid, heptafluorobutanoic acid, nonafluorohexanoic acid, tridecafluorooctanoic acid, heptadecafluorododecanoic acid, or metal salts thereof. As a metal salt, an alkali metal salt or an alkaline earth metal salt is preferred.

As a perfluoroalkyl alcohol, an alcohol having 3 to 41 fluorine atoms and 1 to 20 carbon atoms is preferred. Examples of perfluoroalkyl alcohols include pentafluoroethanol, pentafluoropropanol, heptafluoropropanol, heptafluorobutanol, nonafluorohexanol, tridecafluorooctanol, heptadecafluorododecanol, and ethylene oxide (1 to 20 mol per 1 mol of alcohol) adducts of these alcohols.

Examples of mixtures of two or more of them include a mixture of a perfluoroalkylcarboxylic acid and a perfluoroalkyl alcohol, and, for example, a mixture of pentafluoroethanoic acid and pentafluoroethanol is preferred.

Examples of the surface modifier (B3) having a polysiloxane structure include polydimethylsiloxane; polyether-modified polysiloxanes such as polyoxyethylene-modified polysiloxane and poly(oxyethylene/oxypropylene)-modified polysiloxane; carboxy-modified polysiloxanes; epoxy-modified polysiloxanes; amino-modified polysiloxanes; alkoxy-modified polysiloxanes; and mixtures thereof.

The position of an organic group (modifying group) of a modified silicone such as polyether-modified polysiloxanes, carboxy-modified polysiloxanes, epoxy-modified polysiloxanes, and amino-modified polysiloxanes is not particularly limited, but the position of the organic group may be a side chain of the polysiloxane, both terminals of the polysiloxane, one terminal of the polysiloxane, or combination of a side chain and both terminals of the polysiloxane. Among them, in light of absorption properties, the position is preferably either a side chain of the polysiloxane or combination of a side chain and both terminals of the polysiloxane, and more preferably combination of a side chain and both terminals of the polysiloxane.

Examples of an organic group (modified group) of a polyether-modified polysiloxane include groups containing a polyoxyethylene chain or a poly(oxyethylene-oxypropylene) chain. The number of the oxyethylene units and/or oxypropylene units contained in the polyether-modified polysiloxane is preferably from 2 to 40, more preferably from 5 to 30, even more preferably from 7 to 20, and most preferably from 10 to 15 per one polyether-modified polysiloxane molecule. When the number falls within this range, the absorption properties become further favorable. Also, in the case where an oxyethylene group and an oxypropylene group are contained, the content (mass %) of the oxyethylene group and the oxypropylene group in 100 mass % of the polyether-modified polysiloxane is preferably from 1 mass % to 30 mass %, more preferably from 3 mass % to 25 mass %, and even more preferably from 5 mass % to 20 mass %. When the content of the oxyethylene group and the oxypropylene group falls within the above range, the absorption properties become further favorable.

The polyether-modified polysiloxanes are commercially easily available and, for example, the following commercial products {modification position, type of oxyalkylene} can be preferably exemplified.

Products Manufactured by Shin-Etsu Chemical Co., Ltd:
KF-945 {side chain, oxyethylene and oxypropylene}, KF-6020 {side chain, oxyethylene and oxypropylene}, X-22-6191 {side chain, oxyethylene and oxypropylene}, X-22-4952 {side chain, oxyethylene and oxypropylene}, X-22-4272 {side chain, oxyethylene and oxypropylene}, and X-22-6266 {side chain, oxyethylene and oxypropylene}.

Products Manufactured by Dow Corning Toray Co., Ltd:
FZ-2110 {both terminals, oxyethylene and oxypropylene}, FZ-2122 {both terminals, oxyethylene and oxypropylene}, FZ-7006 {both terminals, oxyethylene and oxypropylene}, FZ-2166 {both terminals, oxyethylene and oxypropylene}, FZ-2164 {both terminals, oxyethylene and oxypropylene}, FZ-2154 {both terminals, oxyethylene and oxypropylene}, FZ-2203 {both terminals, oxyethylene and oxypropylene}, and FZ-2207 {both terminals, oxyethylene and oxypropylene}.

Examples of an organic group (modifying group) of a carboxy-modified polysiloxanes include groups containing a carboxy group, examples of an organic group (modifying group) of an epoxy-modified polysiloxane include groups containing an epoxy group, and examples of an organic group (modifying group) of an amino-modified polysiloxane include groups containing an amino group (primary, secondary, or tertiary amino group). The content (g/mol) of the organic group (modifying group) in each of these modified silicones is preferably from 200 to 11,000, more preferably from 600 to 8,000, and even more preferably from 1,000 to 4,000, as a carboxy equivalent, an epoxy equivalent, or an amino equivalent. If the content falls within this range, the absorption properties become further favorable. It is noted that the carboxy equivalent is measured according to "16. Total Acid Value Test" of JIS C2101:1999. Also, the epoxy equivalent is obtained according to JIS K7236:2001. Moreover, the amino equivalent is measured according to "8. Potentiometric Titration (base value-hydrochloric acid method)" of JIS K2501:2003.

The carboxy-modified polysiloxanes are commercially easily available and, for example, the following commercial products {modification position, carboxy equivalent (g/mol)} can be preferably exemplified.

Products Manufactured by Shin-Etsu Chemical Co., Ltd.:
X-22-3701E {side chain, 4000}, X-22-162C {both terminals, 2300}, and X-22-3710 {one terminal, 1450}.

Products Manufactured by Dow Corning Toray Co., Ltd.:
BY 16-880 {side chain, 3500}, BY 16-750 {both terminals, 750}, BY 16-840 {side chain, 3500}, and SF8418 {side chain, 3500}.

The epoxy-modified polysiloxanes are commercially easily available and, for example, the following commercial products {modification position, epoxy equivalent} can be preferably exemplified.

Products Manufactured by Shin-Etsu Chemical Co., Ltd.:
X-22-343 {side chain, 525}, KF-101 {side chain, 350}, KF-1001 {side chain, 3500}, X-22-2000 {side chain, 620}, X-22-2046 {side chain, 600}, KF-102 {side chain, 3600}, X-22-4741 {side chain, 2500}, KF-1002 {side chain, 4300}, X-22-3000T {side chain, 250}, X-22-163 {both terminals, 200}, KF-105 {both terminals, 490}, X-22-163A {both terminals, 1000}, X-22-163B {both terminals, 1750}, X-22-163C {both terminals, 2700}, X-22-169AS {both terminals, 500}, X-22-169B {both terminals, 1700}, X-22-173DX {one terminal, 4500}, and X-22-9002 {side chain and both terminals, 5000}.

Products Manufactured by Dow Corning Toray Co., Ltd.:
FZ-3720 {side chain, 1200}, BY 16-839 {side chain, 3700}, SF 8411 {side chain, 3200}, SF 8413 {side chain, 3800}, SF 8421 {side chain, 11000}, BY 16-876 {side chain, 2800}, FZ-3736 {side chain, 5000}, BY 16-855D {side chain, 180}, and BY 16-8 {side chain, 3700}.

The amino-modified silicones are commercially easily available and, for example, the following commercial products {modification position, amino equivalent} can be preferably exemplified.

Products Manufactured by Shin-Etsu Chemical Co., Ltd.:
KF-865 {side chain, 5000}, KF-864 {side chain, 3800}, KF-859 {side chain, 6000}, KF-393 {side chain, 350}, KF-860 {side chain, 7600}, KF-880 {side chain, 1800}, KF-8004 {side chain, 1500}, KF-8002 {side chain, 1700}, KF-8005 {side chain, 11000}, KF-867 {side chain, 1700}, X-22-3820W {side chain, 55000}, KF-869 {side chain, 8800}, KF-861 {side chain, 2000}, X-22-3939A {side chain, 1500}, KF-877 {side chain, 5200}, PAM-E {both terminals, 130}, KF-8010 {both terminals, 430}, X-22-161A {both terminals, 800}, X-22-161B {both terminals, 1500}, KF-8012 {both terminals, 2200}, KF-8008 {both terminals, 5700}, X-22-1660B-3 {both terminals, 2200}, KF-857 {side chain, 2200}, KF-8001 {side chain, 1900}, KF-862 {side chain, 1900}, and X-22-9192 {side chain, 6500}.

Products Manufactured by Dow Corning Toray Co., Ltd.:
FZ-3707 {side chain, 1500}, FZ-3504 {side chain, 1000}, BY 16-205 {side chain, 4000}, FZ-3760 {side chain, 1500}, FZ-3705 {side chain, 4000}, BY 16-209 {side chain, 1800}, FZ-3710 {side chain, 1800}, SF 8417 {side chain, 1800}, BY 16-849 {side chain, 600}, BY 16-850 {side chain, 3300}, BY 16-879B {side chain, 8000}, BY 16-892 {side chain, 2000}, FZ-3501 {side chain, 3000}, FZ-3785 {side chain, 6000}, BY 16-872 {side chain, 1800}, BY 16-213 {side chain, 2700}, BY 16-203 {side chain, 1900}, BY 16-898 {side chain, 2900}, BY 16-890 {side chain, 1900}, BY 16-893 {side chain, 4000}, FZ-3789 {side chain, 1900}, BY 16-871 {both terminals, 130}, BY 16-853C {both terminals, 360}, and BY 16-853U {both terminals, 450}.

Examples of mixtures of them include a mixture of polydimethylsiloxane and a carboxyl-modified polysiloxane, and a mixture of a polyether-modified polysiloxane and an amino-modified polysiloxane.

As the surface modifier (B), in light of absorption properties, the surface modifier (B3) having a polysiloxane structure and inorganic fine particles are preferred, and amino-modified polysiloxanes, carboxy-modified polysiloxanes, and silica are more preferred.

The method for treating the crosslinked polymer (A) with the surface modifier (B) is not particularly limited, as long as treatment is conducted such that the surface modifier (B) is present on the surface of the crosslinked polymer (A). However, from the standpoint that the amount of the surface modifier (B) on the surface is controlled, it is preferred that the surface modifier (B) is mixed with a dried product of the crosslinked polymer (A), not with a water-containing gel of the crosslinked polymer (A) or a polymerization liquid that is prior to polymerization of the crosslinked polymer (A). It is noted that it is preferred that the mixing is uniformly conducted.

The shape of the water-absorbent resin powder is not particularly limited, and examples thereof include an indefinite crushed shape, a scale shape, a pearl shape, and a rice grain shape. Among them, the indefinite crushed shape is preferred from the standpoint that the powder in such a shape can be well entangled with fibrous materials in applications such as a disposable diaper and there is little possibility of the powder falling off from the fibrous materials.

The water-absorbent resin powder can be subjected to surface crosslinking where necessary. As a crosslinking agent for conducting the surface crosslinking (a surface crosslinking agent), the same ones as the internal crosslinking agent (b) can be used. In light of absorption performance and the like of the water-absorbent resin powder, the surface crosslinking agent is preferably the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2), more preferably a polyvalent glycidyl, even more preferably ethylene glycol diglycidyl ether and glycerin diglycidyl ether, and most preferably ethylene glycol diglycidyl ether.

In the case of conducting the surface crosslinking, the content (mass %) of the surface crosslinking agent with respect to the total mass (100 mass %) of the water-soluble ethylenically unsaturated monomer (a1) and/or the hydrolyzable monomer (a2), the internal crosslinking agent (b), and the other vinyl monomer (a3) used where necessary is preferably from 0.001 mass % to 7 mass %, more preferably from 0.002 mass % to 5 mass %, and even more preferably 0.003 mass % to 4 mass %. In other words, in this case, the upper limit of the content of the surface crosslinking agent based on the total mass of (a1) and/or (a2), (b), and (a3) is preferably 7 mass %, more preferably 5 mass %, and even more preferably 4 mass % by. Similarly, the lower limit is preferably 0.001 mass %, more preferably 0.002 mass %, and even more preferably 0.003 mass %. If the content of the surface crosslinking agent falls within the above range, the absorption performance becomes further favorable. The surface crosslinking can be achieved by, for example, a method of spraying an aqueous solution containing the surface crosslinking agent to the water-absorbent resin powder or impregnating the water-absorbent resin powder with the aqueous solution containing the surface crosslinking agent, followed by heating treatment (100 to 200 degrees centigrade) on the water-absorbent resin powder.

The water-absorbent resin powder can contain additives such as an antiseptic, a fungicide, an antibacterial, an antioxidant, a ultraviolet absorber, a coloring agent, a perfuming agent, a deodorizer, an inorganic powder, and an organic fibrous material. Examples of such additives include those exemplified in Japanese Patent Publication No. 2003-225565 and Japanese Patent Publication No. 2006-131767. When these additives are contained, the content (mass %) of the additives with respect to the crosslinked polymer (A) (100 mass %) is preferably from 0.001 mass % to 10 mass %, more preferably from 0.01 mass % to 5 mass %, even more preferably from 0.05 mass % to 1 mass %, and most preferably from 0.1 mass % to 0.5 mass %.

The absorbent article of the present invention comprises an absorber composed of at least one absorbent layer, wherein the aforementioned water-absorbent resin powder is disposed in an uppermost layer of the absorber. Since the aforementioned water-absorbent resin powder is disposed in the uppermost layer of the absorber, the absorbent article of the present invention has a high absorption speed, is unlikely to cause a liquid to remain on a skin-contacting surface, has excellent dry feeling, and is unlikely to cause excreted body fluid to return. In addition, as will be described later, when a water-absorbent layer having a high content of the water-absorbent resin powder is used as the uppermost layer of the absorber, an absorbent article is obtained which is less likely to lose its shape as compared to that with a water-absorbent layer having a high fiber content.

The absorbent layer containing the water-absorbent resin powder has a high content of the water-absorbent resin powder and a low content of a fibrous base material in order to make the thinner absorbent layer. In this respect, the content of the water-absorbent resin powder contained in the absorbent layer is preferably 60 mass % or more, more preferably 62 mass % or more, and even more preferably 65 mass % or more. The absorbent layer containing the water-absorbent resin powder may contain a fibrous base material, but in order to make the thinner absorbent layer, the content of the fibrous base material is preferably 20 mass % or less, more preferably 18 mass % or less, and even more preferably 16 mass % or less. In addition, from the standpoint that the absorbent layer is thin, the thickness of the absorbent layer in which the water-absorbent resin powder is disposed is preferably 5 mm or less, more preferably 3 mm or less, and even more preferably 2 mm or less.

Hereinafter, the absorbent article of the present invention will be described with reference to the drawings, but the present invention is not limited to embodiments illustrated in the drawings.

FIGS. 1 and 2 are schematic cross-sectional views illustrating preferred embodiments of the absorber used in the present invention. Each of the absorbers in FIGS. 1 and 2 is composed of only an absorbent layer 1 in which the aforementioned water-absorbent resin powder is disposed. As shown in FIG. 1, the absorbent layer 1 in which the aforementioned water-absorbent resin powder is disposed includes a liquid-permeable first sheet 2, a second sheet 3, and a water-absorbent resin powder 4 disposed between the first sheet 2 and the second sheet 3. The water-absorbent resin powder 4 is fixed to the first sheet 2 and the second sheet 3 by, for example, a hot-melt adhesive (not shown). FIG. 2 is a schematic cross-sectional view of another preferred embodiment of the absorbent layer 1 in which the water-absorbent resin powder is disposed. In this embodiment, the first sheet 2 and the second sheet 3 are attached to each other at a predetermined interval so as to provide water-absorbent resin powder absent regions 5a in which the water-absorbent resin powder 4 is not present and water-absorbent resin powder present regions 5b in which the water-absorbent resin powder 4 is enveloped by the first sheet and the second sheet. The absorbent layer shown in FIG. 2 is obtained by, for example, applying the water-absorbent resin powder 4 onto the second sheet 3 in a streaky manner.

Examples of the structure of the absorber of the absorbent article of the present invention can include an absorber with a single-layer structure composed of only the absorbent layer 1 containing the water-absorbent resin powder 4 as shown in FIGS. 1 and 2; an absorber with a two-layer structure in which the absorbent layer 1 containing the water-absorbent resin powder 4 and another absorbent layer 6 are laminated in order from the skin side (FIGS. 3 and 4); an absorber with a three-layer structure in which the absorbent layer 1 containing the water-absorbent resin powder 4 and other two absorbent layers 6 are laminated in order from the skin side (FIG. 5); and an absorber with a three-layer structure in which another absorbent layer 6 is interposed between two absorbent layers 1 containing the water-absorbent resin powder 4 (FIG. 6). It is noted that in FIGS. 3 to 6, the upper side of the sheet corresponds to the skin side. As shown in FIGS. 3 to 6, the absorber of the absorbent article of the present invention preferably includes, as a lower layer adjacent to the uppermost layer, an absorbent layer 6 containing a water-absorbent resin powder 7 and a fibrous base material (not shown). Since the absorbent layer 6 containing the water-absorbent resin powder 7 and the fibrous base material is disposed as the lower layer, body fluid can be retained in the lower layer and is further unlikely to return to the skin side, and thus dry feeling can be maintained. As the water-absorbent resin powder 7 used in the other absorbent layer 6, the water-absorbent resin powder 4 used in the present invention may be used, or a commercially-available water-absorbent resin powder may be used. In the absorbers shown in FIGS. 4 to 6, the water-absorbent resin powder absent regions 5a in the absorbent layer as the uppermost layer become passages for body fluid, and the body fluid easily passes therethrough to the lower layer. As a result, the absorption speed is further increased, and excellent dry feeling is also provided.

FIG. 7 is a schematic cross-sectional view illustrating a preferred embodiment of the absorbent article of the present invention. An absorbent article 9 includes a liquid-permeable top sheet 10, a liquid-non-permeable back sheet 11, and an absorber between the top sheet 10 and the back sheet 11. Liquid-non-permeable side sheets 12 are joined to upper portions of both side edge portions of the top sheet. The portions of the side sheets 12 inward of joining points 13 form rising flaps which are to rise toward the wearer's skin. The absorber is composed of two absorbent layers 1 and 6. The absorbent layer as the uppermost layer is the absorbent layer 1 which includes a liquid-permeable first sheet 2, a liquid-permeable second sheet 3, and the aforementioned water-absorbent resin powder 4 disposed between the first sheet 2 and the second sheet 3. The lower layer of the absorber is the absorbent layer 6 containing a water-absorbent resin powder 7 and a fibrous base material.

FIG. 8 is a schematic cross-sectional view illustrating a modification of the absorbent article in FIG. 7. In the absorber as the uppermost layer in the embodiment of FIG. 7, the first sheet is not used, and the second sheet 3 is configured to be folded to the upper portions of both edge portions of the absorbent layer 1. In this embodiment, the top sheet 10 of the absorbent article also serves as the first sheet of the absorber.

The top sheet of the absorbent article and the first and second sheets of the absorber are liquid-permeable sheet materials, and, for example, are preferably nonwoven fabrics formed from hydrophilic fibers. The nonwoven fabric used as the liquid-permeable sheet includes, for example, a point-bonded nonwoven fabric, an air-through nonwoven fabric, a spunlace nonwoven fabric, or a spunbond nonwoven fabric. As hydrophilic fibers forming these nonwoven fabrics, cellulose, rayon, cotton, and the like are used. It is noted that as the first sheet, a liquid-permeable nonwoven fabric that is formed from a hydrophobic fiber (e.g., polypropylene, polyethylene, polyester, polyamide, and nylon) whose surface is hydrophilized with a surfactant may be used.

The back sheet of the absorbent article is preferably a liquid-non-permeable sheet. In addition, as the second sheet of the absorber, a liquid-non-permeable sheet may be used depending on the structure of the absorber. As the liquid-non-permeable sheet, a water-repellent or liquid-non-permeable nonwoven fabric (e.g., a spunbond nonwoven fabric, a meltblown nonwoven fabric, and an SMS (spunbond-meltblown-spunbond) nonwoven fabric) formed from a hydrophobic fiber (e.g., polypropylene, polyethylene, polyester, polyamide, and nylon) or a water-repellent or liquid-non-permeable plastic film is used. The liquid-non-permeable sheet prevents moisture and the like of excrement that reaches the liquid-non-permeable sheet, from oozing out of the absorbent article. When a plastic film is used as the liquid-non-permeable sheet, a moisture-permeable (air-permeable) plastic film is preferably used from the standpoint that humid feeling is prevented to improve the wearer's comfort.

Specific examples of the absorbent article of the present invention include a disposable diaper, a sanitary napkin, an incontinence pad, and a breast milk pad.

EXAMPLES

Hereinafter, the present invention will be described in detail by means of examples. However, the present invention is not limited to the examples below, and changes and embodiments that do not depart from the gist of the present invention are included in the scope of the present invention.

<<Evaluation Methods>>

(Method for Measuring Bulk Density)

Measurement of a bulk density is conducted according to JIS K6219-2 2005. A water-absorbent resin powder that is a sample is poured into a center portion of a cylindrical container whose mass and capacity are known (a stainless steel container having a diameter of 100 mm and a capacity of 1000 ml), from a height that is a height of 50 mm or less from the lower end of the container. At that time, a sufficient amount of the sample is poured into the cylindrical container such that the poured sample forms a triangular pyramid above the upper end of the cylindrical container. Then, the excessive sample above the upper end of the cylindrical container is swept down using a spatula, and the mass of the container in this state is measured. The mass of the container itself is subtracted from the measured value to obtain the mass of the sample, and the mass of the sample is divided by the capacity of the container to calculate a bulk density which is an object. The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Method for Measuring Water-Absorption Speed by Vortex Method)

50 mL of a saline (0.9 wt % sodium chloride solution) and a magnetic stir tip (a diameter at center portion: 8 mm, a diameter at both end portions: 7 mm, length: 30 mm, the surface is coated with a fluororesin) are placed into a 100-mL glass beaker, and the beaker is placed on a magnetic stirrer (HPS-100 manufactured by AS ONE Corporation). The rotational speed of the magnetic stirrer is adjusted to 600 plus or minus 60 rpm, and the saline is stirred. 2.0 g of a sample is added to the solution at the center of the vortex of the saline being stirred, and the water-absorption speed (seconds) of the water-absorbent resin powder is measured according to JIS K 7224 (1996). Specifically, a stopwatch is started at the time when the addition of the water-absorbent resin powder, which is the sample, to the beaker is completed. The stopwatch is stopped at the time when the stirrer tip is covered with the test solution (the time when the vortex disappears and the surface of the solution becomes flat), and the time (seconds) is recorded as a water-absorption speed. The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Method for Measuring Liquid-Passing Speed Under Load)

In a 100-mL glass beaker, 0.32 plus or minus 0.005 g of a water-absorbent resin powder that is a sample is immersed in 100 mL of a saline (0.9 wt % sodium chloride solution) and allowed to stand for 60 minutes, thereby swelling the water-absorbent resin powder. Separately, a filtration cylindrical tube is prepared in which a wire mesh (openings: 150 micrometers, a bio-column sintered stainless steel filter 30SUS sold by Sansyo Co., Ltd) and a narrow tube (inner diameter: 4 mm, length: 8 cm) equipped with a cock (inner diameter: 2 mm) are provided at the lower end of an opening portion of a cylinder (inner diameter: 25.4 mm) that stands vertically. All the content within the beaker including the swollen measurement sample is placed into the cylindrical tube in a state where the cock is closed. Next, a cylindrical bar that has a diameter of 2 mm and has, at its end, a wire mesh having openings of 150 micrometers and a diameter of 25 mm is inserted into the filtration cylindrical tube such that the wire mesh comes into contact with the measurement sample, and further a weight is placed such that a load of 2.0 KPa is applied to the measurement sample. In this state, the filtration cylindrical tube is allowed to stand for 1 minute. Then, the cock is opened to allow the solution to flow out, and the time ($T_1$) (seconds) taken until the solution level within the filtration cylindrical tube reaches a 40-mL scale mark from a 60-mL scale mark (i.e., 20 mL of the solution passes) is measured. A liquid-passing speed under a load of 2.0 KPa is calculated from the following equation using the measured time $T_1$ (seconds). It is noted that in the equation, $T_0$ (seconds) is a measured value of a time taken for 20 mL of a saline to pass through the wire mesh in a state where no measurement sample was put in the filtration cylindrical tube.

Liquid-passing speed under load (seconds)=$(T_1-T_0)$

The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Moisture Absorption Blocking Ratio)

10.0 g of a sample is uniformly placed into an aluminum cup having a bottom diameter of 52 mm and a height of 22 mm (a foil container, product number: 107, manufactured by Toyo Aluminium Ecko Products Co., Ltd.), and the cup is kept still in a constant temperature and humidity chamber at 40 degrees centigrade and a relative humidity of 80% RH for 3 hours. Then, the sample is lightly sieved with a 12-mesh wire mesh, the weight of powdered matter of the measurement sample that has caused blocking due to moisture absorption and has not passed through the 12 mesh and the mass of the sample that has passed through the 12 mesh are measured, and a moisture absorption blocking ratio which is an object is calculated according to the following equation.

Moisture absorption blocking ratio (%)=(weight of sample not passing through 12 mesh after being kept still)/(weight of sample not passing through 12 mesh after being kept still+weight of sample passing through 12 mesh after being kept still)×100

The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Method for Measuring Absorption Ratio)

Measurement of an absorption ratio is conducted according to JIS K 7223 (1996). A nylon mesh having openings of 63 micrometers (JIS Z8801-1:2000) is cut into a rectangle having a width of 10 cm and a length of 40 cm and folded in half at a center in its longitudinal direction, and both ends thereof are heat-sealed, to produce a nylon bag having a width of 10 cm (inside dimension: 9 cm) and a length of 20 cm. 1.00 g of a measurement sample is precisely weighted and placed into the produced nylon bag such that the sample is uniform at the bottom of the nylon bag. The nylon bag containing the sample is immersed in a saline. After 60 minutes from start of the immersion, the nylon bag is taken out from the saline, and is hung vertically for 1 hour to drain the nylon bag. Then, the mass (F1) of the sample is measured. In addition, the same operation is conducted without using any sample, and a mass F0 (g) at that time is measured. Then, an absorption ratio which is an object is calculated according to the following equation from these masses F1 and F0 and the mass of the sample.

Absorption ratio (g/g)=$(F_1-F_0)$/mass of sample (Method for Measuring Water-Retaining Capacity)

Measurement of a water-retaining capacity is conducted according to JIS K 7223 (1996). A nylon mesh having openings of 63 micrometers (JIS Z8801-1:2000) is cut into a rectangle having a width of 10 cm and a length of 40 cm and folded in half at a center in its longitudinal direction, and both ends thereof are heat-sealed, to produce a nylon bag having a width of 10 cm (inside dimension: 9 cm) and a length of 20 cm. 1.00 g of a measurement sample is precisely weighted and placed into the produced nylon bag such that the sample is uniform at the bottom of the nylon bag. The nylon bag containing the sample is immersed in a saline. After 60 minutes from start of the immersion, the nylon bag is taken out from the saline, and is hung vertically for 1 hour to drain the nylon bag. Then, the nylon bag is dehydrated using a centrifugal hydroextractor (model H-130C special type, manufactured by Kokusan Co., Ltd.). The dehydrating conditions are 143 G (800 rpm) and 2 minutes. A mass (R1) after the dehydration is measured. In addition, the same operation is conducted without using any sample, and a mass R0 (g) at that time is measured. Then, a water-retaining capacity which is an object is calculated according to the following equation from these masses R1 and R0 and the mass of the sample.

Water-retaining capacity (g/g)=$(R_1-R_0$−mass of sample)/mass of sample (Absorption Speed and Return Amount by Wet Back Method)

A ring (inner diameter: 50 mm, length: 100 mm, weight: 1250 g) for absorption speed measurement was set on the center of an absorbent article to be measured, and 150 ml of an artificial urine was poured thereinto. The time taken until the artificial urine was completely absorbed from start of the pouring was measured to obtain an absorption speed. The absorbent article was allowed to stand for 30 minutes, and then the artificial urine was poured in for the second time. Furthermore, the absorbent article was allowed to stand for 30 minutes and then the artificial urine was poured in for the third time, and the absorbent article was allowed to stand for 30 minutes and then the artificial urine was poured in for the fourth time to obtain an absorption speed for the fourth time. Moreover, after the pouring for the fourth time, the ring for absorption speed measurement was removed. At the time of 30 minutes, a filter paper (manufactured by Toyo Roshi Kaisha, Ltd.) having a diameter of 110 mm was placed on the absorbent article center, a 3.5-kg weight was placed on the filter paper for 30 seconds, and a wet-back amount was measured based on the difference in weight of the filter paper between before and after the test. It is noted the measurement was conducted, wherein the artificial urine, the measuring atmosphere, and the standing atmosphere were at 25 plus or minus 5 degrees centigrade and 65 plus or minus 10% RH.

Synthesis of Water-Absorbent Resin Powder

Synthesis Example 1

155 parts by mass (2.15 parts by mol) of a water-soluble ethylenically unsaturated monomer (a1-1) {acrylic acid, manufactured by Mitsubishi Chemical Corporation, purity: 100%}, 0.6225 parts by mass (0.0024 parts by mol) of an internal crosslinking agent (b1) {pentaerythritol triallyl ether, manufactured by Daiso Co., Ltd.}, and 340.27 parts by mass of deionized water were kept at 1 degree centigrade while being stirred and mixed. After nitrogen was introduced into the mixture to reduce a dissolved oxygen amount to 0.1 ppm or less, 0.31 parts by mass of a 1% aqueous hydrogen peroxide solution, 1.1625 parts by mass of a 1% aqueous ascorbic acid solution, and 2.325 parts by mass of a 0.5% aqueous 2,2'-azobis[2-methyl-N-(2-hydroxyethyl)-propionamide] solution were added and mixed to initiate polymerization. After the temperature of the mixture reached 85 degrees centigrade, the polymerization was conducted at 85 plus or minus 2 degrees centigrade for about 10 hours, to obtain a water-containing gel (1). Next, while 502.27 parts by mass of the water-containing gel (1) was chopped with a mincing machine (12VR-400K manufactured by KIRE ROYAL Co., LTD), 128.42 parts by mass of a 48.5% aqueous sodium hydroxide solution was added and mixed, and further 3 parts by mass of a 1% aqueous ethylene glycol glycidyl ether solution was added and mixed, to obtain a chopped gel (2). Further, the chopped gel (2) was dried with an air-flow band dryer {200 degrees centigrade, wind velocity: 5 m/second} to obtain a dried product. The dried product was pulverized with a juicer-mixer (OSTER-IZER BLENDER manufactured by Oster Co.), and then the particle size thereof was adjusted to 150 micrometers to 710 micrometers using sieves having openings of 150 micrometers and 710 micrometers, to obtain a dried product particle. While 100 parts by mass of the dried product particle was stirred at a high-speed (with a high-speed stirring turbulizer manufactured by Hosokawa Micron Corporation; rotational speed: 2000 rpm), 5 parts by mass of a 2% water/methanol mixed solution (weight ratio of water/methanol=70/30) of ethylene glycol diglycidyl ether was added by spraying and mixed, and the mixture was kept still at 150 degrees centigrade for 30 minutes to achieve surface crosslinking, thereby obtaining a crosslinked polymer (A). With respect to 100 parts by mass of the crosslinked polymer (A), 0.5 part by mass of silica (Aerosil 380 manufactured by Toshin Chemicals Co., Ltd.) and 0.02 part by mass of a carboxy-modified polysiloxane (X-22-3701E manufactured by Shin-Etsu Chemical Co., Ltd.) were used as a surface modifier (B), followed by stirring at 85 degrees centigrade for 60 minutes. The weight average particle size of the obtained resin powder was adjusted to 400 micrometers to obtain a water-absorbent resin powder 1.

Synthetic Example 2

A water-absorbent resin powder 2 was obtained in the same manner as in Synthetic Example 1, except that "the chopped gel (2) was dried with an air-flow band dryer {200 degrees centigrade, wind velocity: 5 m/second}" was changed to "the chopped gel (2) was dried with an air-flow band dryer {150 degrees centigrade, wind velocity: 5 m/second}".

Synthetic Example 3

A water-absorbent resin powder 3 was obtained in the same manner as in Synthetic Example 1, except that "the chopped gel (2) was dried with an air-flow band dryer {200 degrees centigrade, wind velocity: 5 m/second}" was changed to "the chopped gel (2) was dried with an air-flow band dryer {150 degrees centigrade, wind velocity: 2 m/second}".

Synthetic Example 4

A water-absorbent resin powder 4 was obtained in the same manner as in Synthetic Example 3, except that "the weight average particle size of the obtained resin powder was adjusted to 400 micrometers" was changed to "the weight average particle size of the obtained resin powder was adjusted to 530 micrometers".

Synthetic Example 5

A water-absorbent resin powder 5 was obtained in the same manner as in Synthetic Example 2, except that "the weight average particle size of the obtained resin powder was adjusted to 400 micrometers" was changed to "the weight average particle size of the obtained resin powder was adjusted to 320 micrometers".

Synthetic Example 6

A water-absorbent resin powder 6 was obtained in the same manner as in Synthetic Example 1, except that "the weight average particle size of the obtained resin powder was adjusted to 400 micrometers" was changed to "the weight average particle size of the obtained resin powder was adjusted to 280 micrometers".

Synthetic Example 7

A water-absorbent resin powder 7 was obtained in the same manner as in Synthetic Example 2, except that "0.5 part by mass of silica (Aerosil 380 manufactured by Toshin Chemicals Co., Ltd.) and 0.02 part by mass of a carboxy-modified polysiloxane (X-22-3701E manufactured by Shin-Etsu Chemical Co., Ltd.) were used as a surface modifier (B)" was changed to "0.5 part by mass of silica (Aerosil 380 manufactured by Toshin Chemicals Co., Ltd.) was used as a surface modifier (B)".

Synthetic Example 8

A water-absorbent resin powder 8 was obtained in the same manner as in Synthetic Example 2, except that "0.5 part by mass of silica (Aerosil 380 manufactured by Toshin Chemicals Co., Ltd.) and 0.02 part by mass of a carboxy-modified polysiloxane (X-22-3701E manufactured by Shin-Etsu Chemical Co., Ltd.) were used as a surface modifier (B)" was changed to "0.5 part by mass of silica (Aerosil 200 manufactured by Toshin Chemicals Co., Ltd.) was used as a surface modifier (B)".

Synthetic Example 9

A water-absorbent resin powder 9 was obtained in the same manner as in Synthetic Example 2, except that "0.5 part by mass of silica (Aerosil 380 manufactured by Toshin Chemicals Co., Ltd.) and 0.02 part by mass of a carboxy-modified polysiloxane (X-22-3701E manufactured by Shin-Etsu Chemical Co., Ltd.) were used as a surface modifier (B)" was changed to "0.02 part by mass of a carboxy-modified polysiloxane (X-22-3701E manufactured by Shin-Etsu Chemical Co., Ltd.) were used as a surface modifier (B)".

Synthetic Example 10

A water-absorbent resin powder 10 was obtained in the same manner as in Synthetic Example 2, except that "0.5 part by mass of silica (Aerosil 380 manufactured by Toshin Chemicals Co., Ltd.) and 0.02 part by mass of a carboxy-modified polysiloxane (X-22-3701E manufactured by Shin-Etsu Chemical Co., Ltd.) were used as a surface modifier (B)" was changed to "0.02 part by mass of an amino-modified polysiloxane (KF-880 manufactured by Shin-Etsu Chemical Co., Ltd.) was used as a surface modifier (B)".

Comparative Synthetic Example 1

A comparative water-absorbent resin powder 1 was obtained in the same manner as in Synthetic Example 1, except that "the chopped gel (2) was dried with an air-flow band dryer {200 degrees centigrade, wind velocity: 5 m/second}" was changed to "the chopped gel (2) was dried with an air-flow band dryer {120 degrees centigrade, wind velocity: 2 m/second}".

Comparative Synthetic Example 2

A comparative water-absorbent resin powder 2 was obtained in the same manner as in Synthetic Example 1, except that "the weight average particle size of the obtained resin powder was adjusted to 400 micrometers" was changed to "the weight average particle size of the obtained resin powder was adjusted to 600 micrometers".

Comparative Synthetic Example 3

A comparative water-absorbent resin powder 3 was obtained in the same manner as in Synthetic Example 2, except that "the weight average particle size of the obtained resin powder was adjusted to 400 micrometers" was changed to "the weight average particle size of the obtained resin powder was adjusted to 280 micrometers".

Comparative Synthetic Example 4

2 parts of a polyethylene glycol (PEG 200 manufactured by Sanyo Chemical Industries, Ltd.) was added to 100 parts by weight of the water-absorbent resin powder 7, followed by stirring at 85 degrees centigrade for 60 minutes. The weight average particle size of the obtained resin powder was adjusted to 400 micrometers to obtain a comparative water-absorbent resin powder 4.

With regard to the water-absorbent resin powders obtained in Synthetic Examples 1 to 10 and Comparative Synthetic Examples 1 to 4, the measured physical properties are shown in Table 1.

<<Production of Absorbent Layer>>
<Absorbent Layer 1>

A synthetic rubber type hot-melt adhesive was applied onto an air-through nonwoven fabric as a nonwoven fabric. Then, the water-absorbent resin powder 1 was applied thereonto in a streaky manner, a spunlace nonwoven fabric was laminated on the air-through nonwoven fabric to which the above resin powder had been applied, and the obtained laminate was pressed to obtain an absorbent layer 1.

<Absorbent Layers 2 to 10>

Absorbent layers 2 to 10 were obtained in the same manner as for the absorbent layer 1, except that "the water-absorbent resin powder 1" was changed to "the water-absorbent resin powders 2 to 10".

<Comparative Absorbent Layer 1>

A super-thin comparative absorbent layer 1 was obtained in the same manner as for the absorbent layer 1, except that "the water-absorbent resin powder 1" was changed to "the comparative water-absorbent resin powder 1".

<Comparative Absorbent Layers 2 to 4>

Comparative absorbent layers 2 to 4 were obtained in the same manner as for the comparative absorbent layer 1, except that "the comparative water-absorbent resin powder 1" was changed to "the comparative water-absorbent resin powders 2 to 4".

<<Production of Absorbent Articles>>
<Absorbent Article 1>

The liquid permeable air-through nonwoven fabric, the absorbent layer 1, a tissue, and an absorbent layer obtained by mixing the water-absorbent resin powder and pulp are laminated from the top in this order to obtain the absorbent article 1.

<Absorbent Articles 2 to 10>

Absorbent articles 2 to 10 were obtained in the same manner as for the absorbent article 1, except that "the absorbent layer 1" was changed to "the absorbent layers 2 to 10".

<Comparative Absorbent Article 1>

Comparative Absorbent article 1 was obtained in the same manner as for the absorbent article 1, except that "the absorbent layer 1" was changed to "the comparative absorbent layer 1".

TABLE 1

| | Water-absorvent resin powder properties | | | | | | |
|---|---|---|---|---|---|---|---|
| | Bulk Density (g/ml) | Absorption Speed (Sec.) | Absorption Speed under load (Sec.) | Moisture absorption blocking ratio (%) | Absorption ratio (g/g) | Water-retaining capacity (g/g) | Weight average particle size (μm) |
| Water-absorbent resin powder 1 | 0.45 | 24 | 7 | 1 | 44 | 26 | 400 |
| Water-absorbent resin powder 2 | 0.55 | 30 | 5 | 1 | 46 | 28 | 400 |
| Water-absorbent resin powder 3 | 0.62 | 40 | 4 | 1 | 48 | 30 | 400 |
| Water-absorbent resin powder 4 | 0.62 | 49 | 2 | 1 | 48 | 30 | 530 |
| Water-absorbent resin powder 5 | 0.55 | 25 | 10 | 1 | 42 | 24 | 320 |
| Water-absorbent resin powder 6 | 0.45 | 21 | 9 | 1 | 42 | 24 | 280 |
| Water-absorbent resin powder 7 | 0.55 | 28 | 6 | 1 | 46 | 28 | 400 |
| Water-absorbent resin powder 8 | 0.55 | 27 | 7 | 1 | 46 | 28 | 400 |
| Water-absorbent resin powder 9 | 0.55 | 35 | 5 | 1 | 43 | 28 | 400 |
| Water-absorbent resin powder 10 | 0.55 | 35 | 5 | 1 | 43 | 28 | 400 |
| Comparative Water-absorbent resin powder 1 | 0.65 | 44 | 4 | 1 | 46 | 28 | 400 |
| Comparative Water-absorbent resin powder 2 | 0.62 | 52 | 2 | 1 | 49 | 31 | 600 |
| Comparative Water-absorbent resin powder 3 | 0.55 | 18 | 13 | 1 | 46 | 28 | 280 |
| Comparative Water-absorbent resin powder 4 | 0.55 | 40 | 3 | 7 | 46 | 28 | 400 |

<Comparative Absorbent Articles 2 to 4>

Comparative Absorbent articles 2 to 4 were obtained in the same manner as for the comparative absorbent article 1, except that "the comparative absorbent layer 1" was changed to "the comparative absorbent layers 2 to 4".

For evaluating permeability to the obtained absorbent articles, the time taken until an artificial urine was completely absorbed (an absorption speed) was measured. In addition, for evaluating the return property of the absorbers, a return amount was measured by a wet back method. These results are shown in Table 2.

TABLE 2

| | Absorbent | Absorption speed (Sec.) | | Return amount |
|---|---|---|---|---|
| | Article | 1st time | 4th time | (g/sheet) |
| Example 1 | Absorbent article 1 | 19 | 38 | 15 |
| Example 2 | Absorbent article 2 | 25 | 35 | 15 |
| Example 3 | Absorbent article 3 | 27 | 32 | 14 |
| Example 4 | Absorbent article 4 | 31 | 31 | 16 |
| Example 5 | Absorbent article 5 | 32 | 39 | 18 |
| Example 6 | Absorbent article 6 | 16 | 38 | 16 |
| Example 7 | Absorbent article 7 | 23 | 36 | 13 |
| Example 8 | Absorbent article 8 | 21 | 38 | 18 |
| Example 9 | Absorbent article 9 | 24 | 34 | 17 |
| Example 10 | Absorbent article 10 | 24 | 34 | 16 |
| Comparative Example 1 | Comparative Absorbent article 1 | 45 | 70 | 18 |
| Comparative Example 2 | Comparative Absorbent article 2 | 47 | 71 | 33 |
| Comparative Example 3 | Comparative Absorbent article 3 | 31 | 88 | 40 |
| Comparative Example 4 | Comparative Absorbent article 4 | 30 | 38 | 32 |

As is understood from Table 2, the absorbent articles 1 to 10 of the present invention exhibit excellent absorption speeds and anti-return properties as compared to the comparative example absorbent articles 1 to 4. This is thought to be because example absorbent articles 1 to 10 contain the water-absorbent resin powder having specific properties, and thus the permeability and the absorbability of the absorber are improved. On the other hand, the comparative example absorbent articles 1 to 4 exhibit inferior results to the absorbent articles of the present invention.

With regard to the comparative absorbent article 1, the bulk density of the water-absorbent resin powder contained in the uppermost absorbent layer is high, and thus the permeability to the absorber is unlikely to be improved. Accordingly, it is inferred that the results of both the absorption speed for the first time and the absorption speed for the fourth time were inferior. With regard to the comparative absorbent article 2, the absorption speed of the water-absorbent resin powder contained in the uppermost absorbent layer is low, and thus the permeability to the absorber and the return property are unlikely to be improved. Accordingly, it is inferred that the results of the absorption speed for the first time, the absorption speed for the fourth time, and the return property were inferior. With regard to the comparative absorbent article 3, the absorption speed under load of the water-absorbent resin powder contained in the uppermost absorbent layer is low, and thus the permeability to the absorber and the return property are unlikely to be improved. Accordingly, it is inferred that the results of the absorption speed for the fourth time and the return property were inferior. With regard to the comparative absorbent article 4, the moisture absorption blocking ratio of the water-absorbent resin powder contained in the uppermost absorbent layer is high, and thus the return property of the absorber is unlikely to be improved. Accordingly, it is inferred that the result of the return property was inferior.

The present invention includes the following embodiments.

Embodiment 1

An absorbent article comprising an absorber composed of at least one absorbent layer, wherein a water-absorbent resin powder meeting the following requirements (a) to (d) is disposed in an uppermost layer of the absorber:
(a) a bulk density: 0.45 g/ml to 0.62 g/ml;
(b) an absorption speed by a vortex method: 20 seconds to 50 seconds;
(c) a liquid-passing speed under load: 10 seconds or less; and
(d) a moisture absorption blocking ratio: 5% or less.

Embodiment 2

The absorbent article according to embodiment 1, wherein an absorption ratio of the water-absorbent resin powder is from 40 g/g to 55 g/g.

Embodiment 3

The absorbent article according to embodiment 1 or 2, wherein a water-retaining capacity of the water-absorbent resin powder is from 20 g/g to 45 g/g.

Embodiment 4

The absorbent article according to any one of embodiments 1 to 3, wherein the water-absorbent resin powder is obtained by treating, with a surface modifier (B), a crosslinked polymer (A) obtained by polymerizing a monomer composition containing: a water-soluble ethylenically unsaturated monomer (a1) and/or a hydrolyzable monomer (a2) producing the water-soluble ethylenically monomer (a1) by hydrolysis; and an internal crosslinking agent (b).

Embodiment 5

The absorbent article according to embodiment 4, wherein an amount of the surface modifier (B) for the treatment is from 0.001 part by mass to 1 part by mass with respect to 100 parts by mass of the crosslinked polymer (A).

Embodiment 6

The absorbent article according to embodiment 4 or 5, wherein the surface modifier (B) is at least one member selected from the group consisting of an amino-modified polysiloxane, a carboxy-modified polysiloxane, and silica.

Embodiment 7

The absorbent article according to any one of embodiments 1 to 6, wherein the uppermost absorbent layer has plurality of water-absorbent resin powder present regions in which the water-absorbent resin powder is enveloped and a water-absorbent resin powder absent region adjacent to the water-absorbent resin powder present regions.

Embodiment 8

The absorbent article according to any one of embodiments 1 to 7, further comprising an absorbent layer including an water-absorbent resin powder and a fibrous base material as a lower layer adjacent to the uppermost layer.

INDUSTRIAL APPLICABILITY

The present invention is useful as an absorbent article such as an incontinence pad, a disposable diaper, a sanitary napkin, and a breast milk pad.

REFERENCE SIGNS LIST

1: absorbent layer, 2: first sheet, 3: second sheet, 4: water-absorbent resin powder, 5a: water-absorbent resin absent region, 5b: water-absorbent resin present region, 6: absorbent layer, 7: water-absorbent resin powder, 9: absorbent article, 10: top sheet, 11: back sheet, 12: side sheet, 13: joining point, 14: elastic member

The invention claimed is:

1. A disposable diaper comprising an absorber composed of at least one absorbent layer, wherein a water-absorbent resin powder meeting the following requirements (a) to (e) is disposed in an uppermost layer of the absorber:
   (a) a bulk density: 0.45 g/ml to 0.62 g/ml;
   (b) an absorption speed by a vortex method: 20 seconds to 50 seconds;
   (c) a liquid-passing speed under load: 10 seconds or less; and
   (d) a moisture absorption blocking ratio: 5% or less,
   (e) a water-retaining capacity measured according to JIS K 7223(1996): 20 g/g to 30 g/g,
   wherein the water-absorbent resin powder is obtained by treating, with a surface modifier (B), a crosslinked polymer (A) obtained by polymerizing a monomer composition containing: a water-soluble ethylenically unsaturated monomer (a1) and/or a hydrolyzable monomer (a2) producing the water-soluble ethylenically monomer (a1) by hydrolysis; and an internal crosslinking agent (b), and
   wherein the surface modifier (B) includes at least one member selected from the group consisting of a polydimethylsiloxane, a polyether-modified polysiloxane, a carboxy-modified polysiloxane, an epoxy-modified polysiloxane, an amino-modified polysiloxane and an alkoxy-modified polysiloxane, and
   wherein the surface modifier (B) includes at least one member selected from the group consisting of the carboxy-modified polysiloxane, the epoxy-modified polysiloxane, and the amino-modified polysiloxane, and
   wherein the modifying group in each of these modified silicones has a content of from 200 g/mol to 11,000 g/mol, as a carboxy equivalent, an epoxy equivalent, or an amino equivalent.

2. The disposable diaper according to claim 1, wherein an absorption ratio of the water-absorbent resin powder is from 40 g/g to 55 g/g.

3. The disposable diaper according to claim 1, wherein an amount of the surface modifier (B) for the treatment is from 0.001 part by mass to 1 part by mass with respect to 100 parts by mass of the crosslinked polymer (A).

4. The disposable diaper according to claim 1, wherein the surface modifier (B) includes at least one member selected from the group consisting of the amino-modified polysiloxane, and the carboxy-modified polysiloxane.

5. The disposable diaper according to claim 1, wherein the uppermost absorbent layer has a plurality of water-absorbent resin powder present regions in which the water-absorbent resin powder is enveloped and a water-absorbent resin powder absent region adjacent to the water-absorbent resin powder present regions.

6. The disposable diaper according to claim 1, further comprising an absorbent layer including an water-absorbent resin powder and a fibrous base material as a lower layer adjacent to the uppermost layer.

7. The disposable diaper according to claim 1, wherein the internal crosslinking agent (b) contains tetraallyloxyethane and/or pentaerythritol triallyl ether.

8. The disposable diaper according to claim 1, wherein a weight average particle size of the crosslinked polymer (A) is from 100 micrometers to 800 micrometers.

9. The disposable diaper according to claim 1, wherein a content of fine particles having a size of 106 micrometers or less in the entire particles of the crosslinked polymer (A) is 3 weight % or less.

10. The disposable diaper according to claim 1, wherein a content of the water-absorbent resin powder contained in the uppermost layer of the absorber is 60 mass % or more.

11. The disposable diaper according to claim 1, wherein a thickness of the uppermost layer of the absorber is 5 mm or less.

* * * * *